(12) United States Patent
Yaron

(10) Patent No.: US 7,116,352 B2
(45) Date of Patent: Oct. 3, 2006

(54) CAPSULE

(75) Inventor: Avi Yaron, Givat Shmuel (IL)

(73) Assignee: Visionsense Ltd., Petah Tikva (IL)

( * ) Notice: Subject to any disclaimer, the term of this patent is extended or adjusted under 35 U.S.C. 154(b) by 0 days.

(21) Appl. No.: 09/785,512

(22) Filed: Feb. 16, 2001

(65) Prior Publication Data

US 2001/0017649 A1    Aug. 30, 2001

Related U.S. Application Data

(63) Continuation-in-part of application No. 09/699,624, filed on Oct. 30, 2000, and a continuation-in-part of application No. 09/257,850, filed on Feb. 25, 1999.

(51) Int. Cl.
*H04N 13/00*    (2006.01)

(52) U.S. Cl. .......................... 348/45; 348/49; 348/65; 348/68; 348/70; 348/69; 348/77; 600/112; 600/111; 600/109; 600/110; 600/118

(58) Field of Classification Search ............... 375/130; 348/43, 45, 65, 49, 57, 42, 46, 51, 61, 66, 348/69, 70, 71, 68, 77; 359/824, 813, 826; 600/112, 113, 111, 109, 110, 118
See application file for complete search history.

(56) References Cited

U.S. PATENT DOCUMENTS

| | | | | |
|---|---|---|---|---|
| 2,639,653 A | 5/1953 | Fischer | ............................ | 95/18 |
| 4,414,470 A | 11/1983 | Nakaoka | ...................... | 250/204 |
| 4,437,764 A | 3/1984 | Levine et al. | .................. | 358/44 |
| 4,605,009 A * | 8/1986 | Pourcelot et al. | ............ | 600/109 |
| 4,873,572 A | 10/1989 | Miyazaki et al. | .............. | 358/98 |
| 4,959,641 A | 9/1990 | Bass et al. | ................... | 340/700 |
| 5,034,805 A | 7/1991 | Ishizaka | ....................... | 358/44 |
| 5,076,687 A * | 12/1991 | Adelson | ......................... | 356/4 |
| 5,121,452 A | 6/1992 | Stowe et al. | | |
| 5,192,969 A | 3/1993 | Igarashi et al. | | |
| 5,233,416 A | 8/1993 | Inoue | ........................... | 358/98 |
| 5,428,386 A | 6/1995 | D'Alfonso et al. | ........... | 348/45 |
| 5,490,015 A * | 2/1996 | Umeyama et al. | .......... | 359/824 |
| 5,527,263 A | 6/1996 | Zobel et al. | ................. | 600/166 |
| 5,552,840 A | 9/1996 | Ishii et al. | ................... | 348/751 |
| 5,588,948 A | 12/1996 | Takahashi et al. | ........... | 600/111 |
| 5,594,497 A | 1/1997 | Ahern et al. | ................... | 348/71 |
| 5,603,687 A | 2/1997 | Hori et al. | ................... | 600/166 |
| 5,604,531 A * | 2/1997 | Iddan et al. | ................... | 348/76 |
| 5,606,436 A | 2/1997 | Shapiro | | |

(Continued)

FOREIGN PATENT DOCUMENTS

JP    2001170002 A  *  6/2001

(Continued)

*Primary Examiner*—Shawn S. An
(74) *Attorney, Agent, or Firm*—Merchant & Gould P.C.

(57) ABSTRACT

System for producing a stereoscopic image of an object, and displaying the stereoscopic image, the system including a capsule and a control unit, the capsule including a sensor assembly, a processor connected to the sensor assembly, a capsule transceiver connected to the processor, a light source, and a power supply for supplying electrical power to the capsule transceiver, the processor, the light source and to the sensor assembly, the control unit including a control unit transceiver, and an image processing system connected to the control unit transceiver, wherein, the sensor assembly detects the stereoscopic image, the processor captures the stereoscopic image, the capsule transceiver transmits the stereoscopic image to the control unit transceiver and the image processing system processes the stereoscopic image.

20 Claims, 32 Drawing Sheets

U.S. PATENT DOCUMENTS

| | | | |
|---|---|---|---|
| 5,606,455 A | 2/1997 | Eichenlaub | 359/463 |
| 5,613,936 A | 3/1997 | Czarnek et al. | 600/166 |
| 5,653,677 A * | 8/1997 | Okada et al. | 348/45 |
| 5,743,846 A | 4/1998 | Takahashi et al. | 600/166 |
| 5,743,847 A | 4/1998 | Nakamura et al. | 600/166 |
| 5,751,341 A | 5/1998 | Chaleki et al. | 348/65 |
| 5,760,827 A | 6/1998 | Faris | 348/42 |
| 5,776,049 A | 7/1998 | Takahashi | 600/111 |
| 5,800,341 A | 9/1998 | McKenna | 600/109 |
| 5,812,187 A * | 9/1998 | Watanabe | 348/70 |
| 5,825,534 A | 10/1998 | Strähle | 359/376 |
| 5,828,487 A | 10/1998 | Greening et al. | 359/466 |
| 5,865,829 A | 2/1999 | Kitajima | |
| 5,868,664 A | 2/1999 | Speier et al. | 600/112 |
| 5,966,168 A | 10/1999 | Miyazaki | |
| 5,991,074 A | 11/1999 | Nose et al. | 359/465 |
| 6,075,555 A * | 6/2000 | Street | 348/43 |
| 6,306,082 B1 | 10/2001 | Takahashi et al. | |

FOREIGN PATENT DOCUMENTS

| | | |
|---|---|---|
| WO | WO 00/22975 | 10/1999 |

* cited by examiner

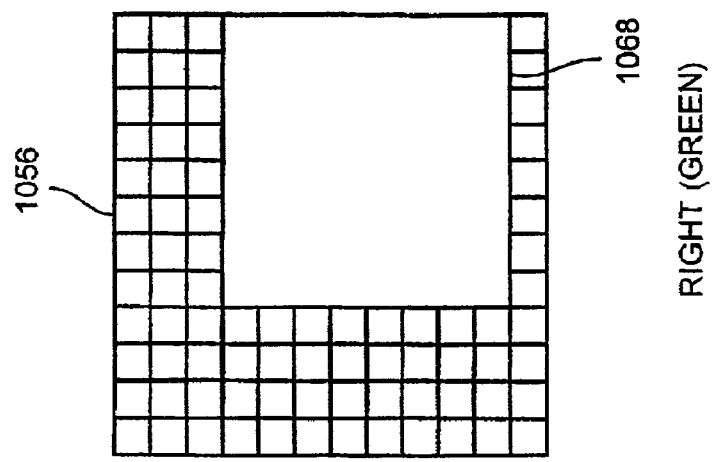
FIG. 27C RIGHT (GREEN)
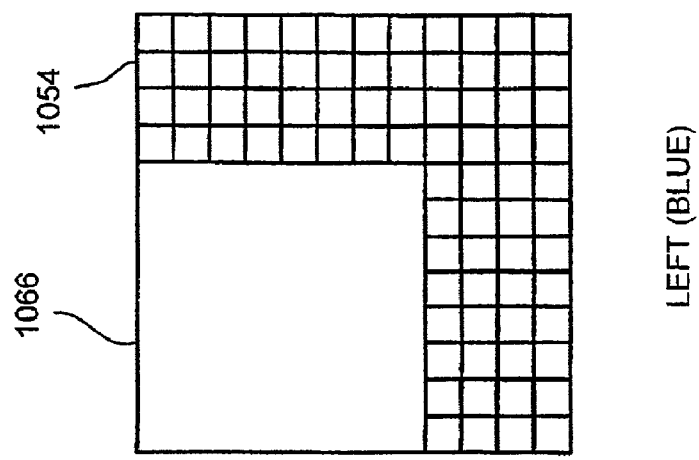
FIG. 27B LEFT (BLUE)
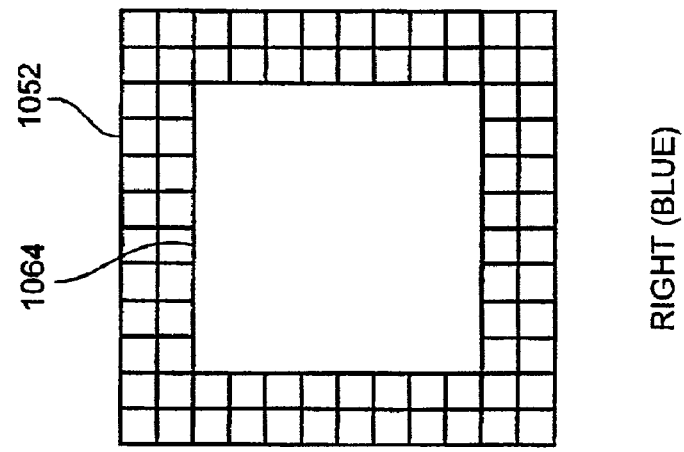
FIG. 27A RIGHT (BLUE)

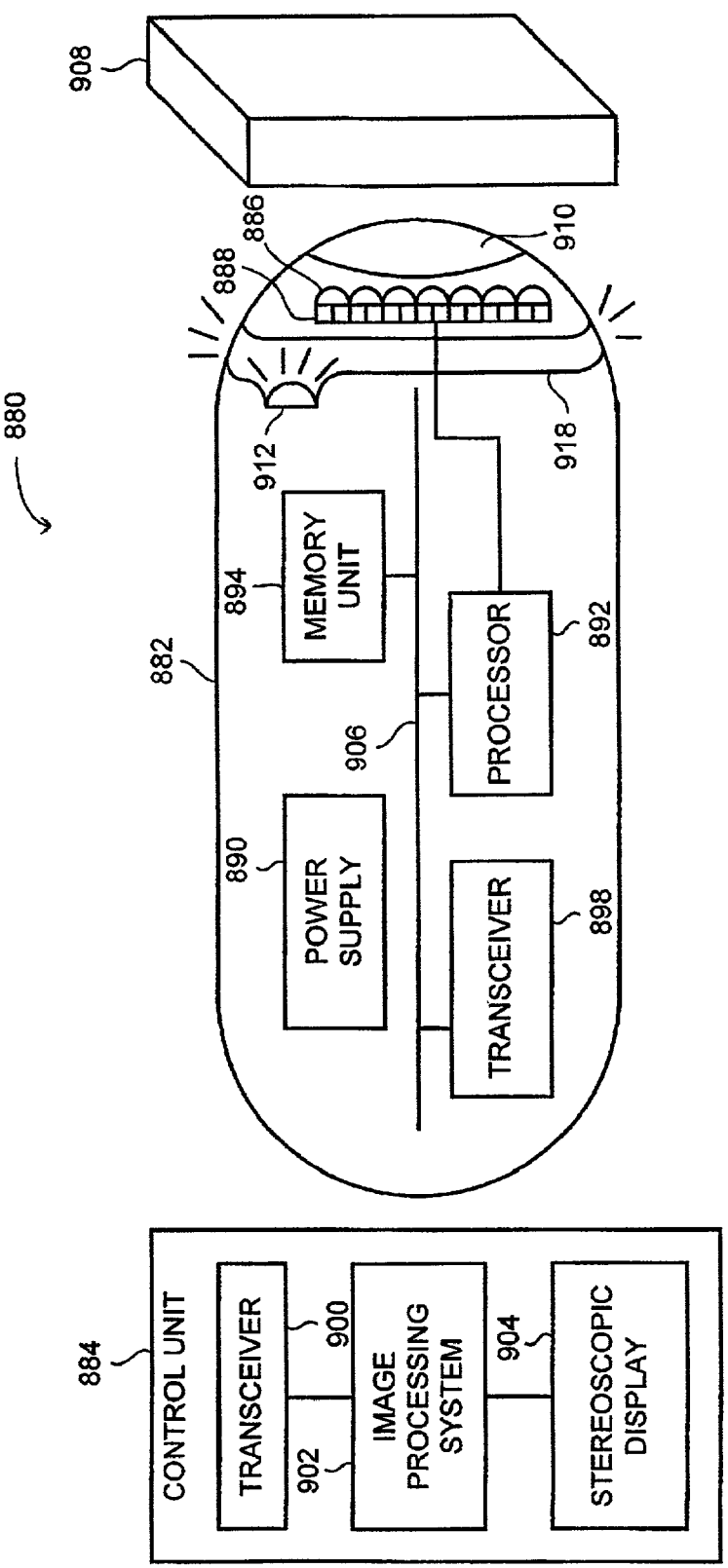

CAPSULE

CROSS REFERENCE INFORMATION

This application is a Continuation-in-Part of application Ser. No. 09/257,850, filed Feb. 25, 1999 and Ser. No. 09/699,624, filed Oct. 30, 2000.

FIELD OF THE INVENTION

The present invention relates to endoscopes, microscopes and boroscopes, in general and to stereoscopic image pick up devices with color imaging capability, in particular.

BACKGROUND OF THE INVENTION

Stereoscopic image detection devices are known in the art. Such devices are required to obtain and provide a combination of small cross section and high image quality. It will be appreciated by those skilled in the art that high image quality, in general, is characterized by stereoscopic vision accuracy, color capabilities, high resolution and illumination requirements.

It is noted that conventional methods, which provide stereoscopic images, require a wider optical path than a monocular one. Such a widened optical path enlarges the cross-section required for the detection device considerably. Hence, the requirement for a small cross section is not maintained.

U.S. Pat. No. 5,527,263 to Zobel et al., is directed to a dual optical path stereo endoscope with simple optical adjustment. U.S. Pat. No. 5,776,049 to Takahashi, is directed to a "Stereo Endoscope Imaging Apparatus" and provides a device which utilizes a combination of two optical paths with two CCD units, capable of variable zoom.

Auto-stereoscopic devices, which utilize one optical system to provide a stereo effect, are also known in the art. Such a device is provided in U.S. Pat. No. 5,603,687 to Hori et al., which is directed to a device with two parallel optical axis and two CCD elements. Hori selected an asymmetrical approach, wherein one optical channel has a large aperture for light and details and the other optical channel provides a parallax image for stereoscopic imagery to the proximal CCD.

U.S. Pat. No. 5,613,936 to Czarnek et al., is directed to a stereoscopic endoscope device which utilizes light polarization and time multiplexing in order to transmit each different polarized image corresponding to left and right images multiplexed in time, through one optical channel that transfers images from the lateral side of the endoscope shaft. This endoscope has to be inserted deeper into the human cavity to receive a stereo image. It must also be used with a head mounted display device called "switched shutter glasses" that causes eye irritation. It is noted that according to Czarnek each image is received in 25% of original quality. As much as 50% of the light received fro the object, is lost due to polarization considerations and as much as 50% of the remaining information is lost due to channel switching.

U.S. Pat. No. 5,588,948, to Takahashi et al., is directed to a Stereoscopic Endoscope. The stereo effect is produced by having a dividing pupil shutter, which splits the optical path onto the left and right sides, and the up and down sides. These sides are alternatively projected on a proximal image pickup device, using time multiplexing. According to another aspect of this reference includes a distal CCD, which is divided to left and right sides with a shading member separating them, for achieving space multiplexing.

U.S. Pat. No. 5,743,847 to Nakamura et al., is directed to a "Stereoscopic Endoscope Having Image Transmitting Optical-System and Pupil Dividing Unit that are Axially Movable With Respect to Each Other", which uses a plural pupil dividing means and one optical channel. U.S. Pat. No. 5,751,341 to Chaleki et al., is directed to a "Stereoscopic Endoscope System", which is basically a two channel endoscope, with one or two proximal image sensors. A rigid sheath with an angled distal tip could be attached to its edge and be rotated, for full view.

U.S. Pat. No. 5,800,341 to Mckenna et al, who is directed to an "Electronically Steerable Endoscope", which provides different fields of view, without having to move the endoscope, using a plurality of CCD cells and processing means. U.S. Pat. No. 5,825,534 to Strahle, is directed to a "Stereo Endoscope having a Folded Sight Line" including stereo-endoscope optical channel, having a sight line folded relative to tube axis.

U.S. Pat. No. 5,828,487 to Greening et al., is directed to a "Stereoscopic Viewing System Using a Two Dimensional Lens System" which in general, provides an alternative R-L switching system. This system uses a laterally moving opaque leaf, between the endoscope and the camera, thus using one imaging system. U.S. Pat. No. 5,594,497 to Ahern, describes a distal color CCD, for monocular view in an elongated tube.

The above descriptions provide examples of auto-stereoscopic inventions, using different switching techniques (Time division multiplexing) and polarization of channels or pupil divisions (spatial multiplexing), all in an elongated shaft. When color image pick up devices are used within these systems, the system suffers from reduced resolution, loss of time related information or a widened cross section.

The issue of color imagery or the issue of a shaft-less endoscope is not embedded into any solution. To offer higher flexibility and to reduce mechanical and optical constraints it is desired to advance the image pick-up device to the frontal part of the endoscope. This allows much higher articulation and lends itself easily to a flexible endoscope. Having a frontal pick up device compromises the resolution of the color device due to size constraints (at this time).

U.S. Pat. No. 5,076,687 to Adelson, is directed to an "Optical Ranging Apparatus" which is, in general a depth measuring device utilizing a lenticular lens and a cluster of pixels.

U.S. Pat. No. 5,760,827 to Faris, is directed to "Pixel Data Processing System and Method for Producing Spectrally-Multiplexed Images of Three-Dimensional Imagery for Use in Stereoscopic Viewing Thereof" and demonstrates the use of multiplexing in color and as such, offers a solution for having a color stereo imagery with one sensor. Nevertheless, such a system requires several sequential passes to be acquired from the object, for creating a stereo color image.

U.S. Pat. No. 5,812,187 to Watanabe, is directed to an Electronic Endoscope Apparatus. This device provides a multi-color image using a monochromatic detector and a mechanical multi-wavelength-illuminating device. The monochromatic detector detects an image, each time the multi-wavelength-illuminating device produces light at a different wavelength.

U.S. Pat. No. 5,604,531 issued to Iddan, et al., and entitled "In Vivo Video Camera System", is directed to a system for viewing the inside of the digestive system of a patient. The system includes a swallowable capsule, which views the inside of the digestive system and transmits video data, a reception system located outside the patient, and a data processing the video data. The capsule includes a light source, a window, a camera system such as a CCD camera, an optical system, a transmitter, and a power source.

The light source illuminates the inner portions of the digestive system through the window. The camera system detects the images, the optical system focuses the images onto the CCD camera, the transmitter transmits the video signal of the CCD camera, and the power source provides power to the electrical elements of the capsule. The CCD camera can provide either black and white or color signals. The capsule can additionally include sensor elements for measuring pH, temperature and pressure.

International publication No. WO 00/22975 entitled "A Method For Delivering a Device to a Target Location", is directed to a method for viewing the inside of the digestive system, and discharging medicaments or collecting fluid or cell samples from the environment. The method employs a capsule, which includes a light source, a viewing window, a camera system, an optical system, a transmitter, a power source, and a storage compartment for releasing a medicament or collecting cell samples or fluid. The light source, viewing window, camera system, optical system, transmitter, and power source are similar to those described herein above in connection with U.S. Pat. No. 5,604,531.

One end of the capsule includes a bi-stable spring connected between an inflexible barrier proximal to the capsule and a firm diaphragm distal to the capsule, thus forming the storage compartment. The capsule includes a pouch wall between the firm diaphragm and the capsule end. The firm diaphragm includes a piercing pin for rupturing the pouch wall. The capsule end furthermore includes a permeable area for transfer of fluid to or from the storage compartment.

The spring is extended by heating it, thus moving the firm diaphragm distally. The piercing pin ruptures the pouch wall, thereby allowing controllable amount of the medicament to exit from the storage compartment through the hole pierced in the pouch wall and through the permeable area. Conversely, the bi-stable spring is retracted in order to collect a controllable amount of fluid or cell samples, wherein the fluid transfers to the storage compartment, through the permeable area.

SUMMARY OF THE PRESENT INVENTION

It is an object of the present invention to provide a novel system for stereoscopic imaging using a lenticular lens layer and a sensor array, and a novel method for operating the same, which overcomes the disadvantages of the prior art.

In accordance with the present invention, there is thus provided a stereoscopic device, which includes a lenticular lens layer and a color light sensor array. The lenticular lens layer includes a plurality of lenticular elements. Each of the lenticular elements is located in front of a selected group of the light sensors of the sensor array, thereby directing light from different directions to different light sensors within the selected group of the light sensors.

In accordance with a further aspect of the invention, there is provided a stereoscopic device, which includes a lenticular lens layer and a light sensor array, including a plurality of light sensors, where each of the light sensors detects light at a predetermined range of wavelengths.

The stereoscopic device according to the invention can be constructed as a large-scale device, such as a television camera or a small-scale device such as an endoscope.

In a stereoscopic device according to the invention, each of the lenticular elements includes light directing means, which distinguish between at least two directions of light. For example, each of the lenticular elements can be shaped in a general semi-cylindrical shape. Each of the lenticular elements can alternatively include light directing means, which distinguish between four directions of light. For example, such a lenticular element can be shaped in a general semispherical shape.

According to one aspect of the invention, each of the selected groups of the light sensors includes an even number of light sensors. According to another aspect of the invention, each of the selected groups of the light sensors includes an odd number of light sensors.

The stereoscopic device of the invention can further include an illuminating unit. This light illuminating unit can surround the lenticular lens layer. An illumination unit according to the invention includes a light source, a light distribution unit and light guiding means connected between the light source and the light dispersing unit. The light guiding means guides light from the light source to the light dispersing unit. According to one aspect of the invention, the light dispersing unit surrounds the lenticular lens layer.

The light illuminating unit can produce light in a predetermined range of wavelengths. According to another aspect of the invention, the light illuminating unit produces at least two alternating beams of light, where each of the beams of light is characterized as being in a different range of wavelengths.

The stereoscopic device according to the invention, can further include a controller connected to the array of light sensors. This controller produces an image for each of the different directions, by combining data received from the light sensors respective of each of the different directions.

This controller can be connected to the array of light sensors. Accordingly, the controller produces an image for each combination of a selected one, of the different directions and a selected one of the beams of light, by combining data received from the light sensors respective of each of the different directions, with respect to the currently illuminating one of the beams of light.

The stereoscopic device according to the invention can further include capturing means, connected to the array of light sensors, for capturing data received from light sensors and a storage unit for storing the captured data. The stereoscopic device can further include a stereoscopic display unit, connected to the controller, for producing the image in a stereoscopic manner. The produced image can be partially stereoscopic.

The predetermined ranges of wavelengths, which are applicable for the light sensors as well as for the illumination light beams can be substantially visible red color light, substantially visible green color light, substantially visible blue color light, substantially visible cyan color light, substantially visible yellow color light, substantially visible magenta color light, substantially infra-red light, substantially ultra-violet light, visible light, and the like.

For example, either the light sensor array or the light beams can include a color combination of red-green-blue (RGB), cyan-yellow-magenta-green (CYMG), a white light color combination, and the like.

In accordance with a further aspect of the invention, there is thus provided a method for detecting a stereoscopic image. The method includes the steps of splitting light which arrives from different directions, using a lenticular lens layer, thereby producing at least two images, which are intertwined in a master image, and detecting the master image.

The method can further include the step of reconstructing each of the images from the master image. In addition, the method can further include the step of displaying the images using a stereoscopic display device.

Furthermore, the method can include the step of simultaneously displaying the images on a stereoscopic display device. In addition, the method can further include the steps of sequentially illuminating a detected area with alternating beams of light of different ranges of wavelength, and associating the master image in time, with the currently illuminating ranges of wavelength.

The step of reconstructing can include the steps of determining a range of wavelengths for each pixel within each one of the images, and determining an intensity level for each pixel within each one of the images. The step of reconstructing can further include the steps of selecting one of the pixels, associated with a predetermined range of wavelengths and determining the pixels associated with another range of wavelengths, in the vicinity of the selected pixel. The step of reconstructing can further include the steps of calculating an approximated level of the other range of wavelengths at the location of the selected pixel and starting again from the step of selecting.

In accordance with another aspect of the present invention, there is thus provided a stereoscopic device for detecting a stereoscopic image. The stereoscopic device includes at least two apertures, a multi wavelength light sensor array and a controllable multi wavelength illumination unit. Each aperture includes a plurality of light valves. The controllable multi wavelength illumination unit produces at least two alternating beams of light, where each beam of light is characterized as being in a different range of wavelengths. Each light valve is operative to open at a different predetermined timing. Furthermore, the multi wavelength light sensor array detects a plurality of images, where each of the images corresponds to a predetermined combination of an open state of a selected light valve and a selected mode.

In accordance with a further aspect of the present invention, there is thus provided a method for detecting a stereoscopic image. The method includes the steps of alternating between at least two apertures, producing a sequence of at least two illumination beams and detecting a plurality of frames. The apertures are directed at an object. The illumination beams are produced in different ranges of wavelengths. Each of the frames is detected for a combination, which includes a selected aperture and a selected illumination beam.

In accordance with another aspect of the present invention, there is thus provided a stereoscopic device. The stereoscopic device includes a sensor assembly for detecting a sequence of stereoscopic images of an object, a movement detector for detecting the movements of the sensor assembly relative to the object, and a processing unit connected to the sensor assembly and to the movement detector. The processing unit selects portions of the stereoscopic images, according to a signal received from the movement detector, thereby producing a visually stable sequence of display images.

In accordance with a further aspect of the present invention, there is thus provided a method for producing a stable sequence of stereoscopic images of an object. The method includes the steps of detecting a plurality of stereoscopic images, for each of the stereoscopic images, detecting the movements of the stereoscopic sensor assembly relative to the object, and for each the stereoscopic images, selecting a portion of each of the stereoscopic images, according to the respective movement. The stereoscopic images are detected by employing a stereoscopic sensor assembly.

In accordance with another aspect of the present invention, there is thus provided a system for producing a stereoscopic image of an object and displaying the stereoscopic image. The system includes a capsule and a control unit. The capsule includes a sensor assembly, a processor connected to the sensor assembly, a capsule transceiver connected to the processor, a light source, and a power supply. The power supply supplies electrical power to the capsule transceiver, the processor, the light source and to the sensor assembly. The control unit includes a control unit transceiver, and an image processing system connected to the control unit transceiver. The sensor assembly detects the stereoscopic image, the processor captures the stereoscopic image, the capsule transceiver transmits the stereoscopic image to the control unit transceiver and the image processing system processes the stereoscopic image.

BRIEF DESCRIPTION OF THE DRAWINGS

The present invention will be understood and appreciated more fully from the following detailed description taken in conjunction with the drawings in which:

FIG. 27A is a schematic illustration of a sub-matrix, in accordance with another preferred embodiment of the present invention, when the sensor assembly is at a location illustrated in FIG. 25A;

FIG. 27B is a schematic illustration of a sub-matrix, when the sensor assembly is at a location illustrated in FIG. 25B;

FIG. 27C is a schematic illustration of a sub-matrix, when the sensor assembly is at a location illustrated in FIG. 25C;

FIG. 28 is a schematic illustration of an imaging system, constructed and operative in accordance with a further preferred embodiment of the present invention;

DETAILED DESCRIPTION OF PREFERRED EMBODIMENTS

The present invention overcomes the disadvantages of the prior art by providing a continuous vision stereoscopic apparatus, using a generally lenticular lens layer, a light sensor array and an image processing system.

Figure 1:
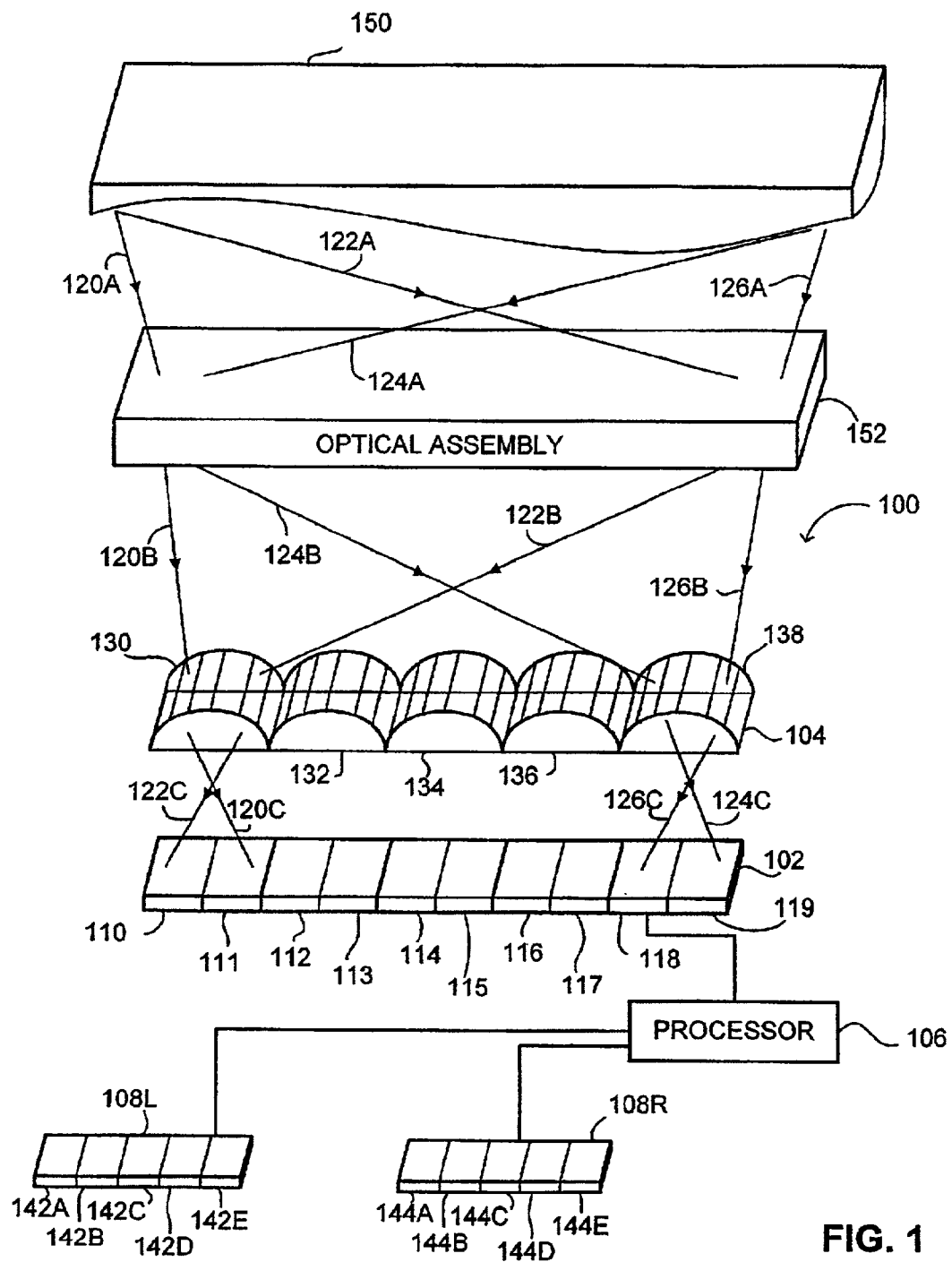
FIG. 1 is a schematic illustration of a three dimensional object and a stereoscopic vision apparatus, constructed and operative in accordance with a preferred embodiment of the present invention.

Reference is now made to FIG. 1, which is a schematic illustration of a three dimensional object and a stereoscopic vision apparatus, generally referenced 100, constructed and operative in accordance with a preferred embodiment of the present invention. Apparatus 100 includes a lenticular lens layer 104, a light sensor array 102, a processor 106 and two display devices 108R and 108L. Apparatus 100 is placed in front of a three-dimensional object 150. An optical assembly 152 is placed between apparatus 100 and object 150, for focusing the image of object 150 on light sensor array 102.

Light sensor array 102 includes a plurality of sensors 110, 111, 112, 113, 114, 115, 116, 117, 118 and 119. Lenticular lens layer 104 includes a plurality of lenticular elements 130, 132, 134, 136 and 138. Each one of the lenticular elements is located above two light sensors, in a way that lenticular element 130 is located above sensors 110 and 111, lenticular element 132 is located above sensors 112 and 113, lenticular element 134 is located above sensors 114 and 115, lenticular element 136 is located above sensors 116 and 117 and lenticular element 138 is located above sensors 118 and 119.

The light sensors 110, 111, 112, 113, 114, 115, 116, 117, 118, and 119, detect light as directed by the lenticular lens elements 130, 132, 134, 136 and 138, and provide respective information to the processor 106. The processor 106 processes this information, produces a pair of images, as will be explained in detail herein below, and provides them to the display units 108R and 108L, which in turn produce visual representations of these images.

In general, each lenticular element directs light rays, which arrive from a predetermined direction to a predetermined location, and light rays which arrive from another predetermined direction, to another predetermined location. Hence, the present invention, utilizes the lenticular lens layer to distinguish between a right view image and a left view image, as is described herein below.

Each of the display units 108R and 108L includes a plurality of display units also known as pixels. Display unit 108L includes pixels 142A, 142B, 142C, 142D and 142E. Display unit 108R includes pixels 144A, 144B, 144C, 144D and 144E. Using these pixels each of the display units 108R and 108L produces an image, according to data provided from the processor 106. The two images, each viewed by a different eye of the user, produce a sensation of a three dimensional image.

Light rays 124A, and 126A represent a right-side image of the three dimensional object 150. Light rays 120A, and 122A represent a left side image of the three-dimensional object 150. The optical assembly 152 redirects light rays 120A, 122A, 124A and 126A so as to focus them on a plain which is determined by the light sensor array 102, as light rays 120B, 122B, 124B and 126B, respectively. Hence, light rays 122B and 126B represent a focused right side view of the three-dimensional object 150, and light rays 120B and 124B represent a focused left side view of the three-dimensional object 150.

The lenticular lens layer 104 directs the focused right side view light rays 122B and 126B to light sensors 110 and 118, respectively, as respective light rays 122C and 126C. In addition, the lenticular lens layer 104 directs the focused left side view light rays 120B and 124B to light sensors 111 and 119, respectively. In general, light sensors 111, 113, 115, 117 and 119 detect light rays which relate to a left side view image of object 150, and light sensors 110, 112, 114, 116, and 118, detect light rays which relate to a right side view image of object 150.

Hence, light sensors 110, 112, 114, 116 and 118 detect the right side image of object 150, while light sensors 111, 113, 115, 117 and 119 detect the left side image of object 150. The light sensor array 102 provides data relating to the detected light intensity at each of the light sensors to the processor 106.

The processor 106 processes this data, produces a right side image from the data relating to the right side view and a left side image from the data relating to the left side view, and provides the respective image to the respective display unit 108R and 108L. In the present example, the processor 106 utilizes the data received from sensors 110, 112, 114, 116 and 118 to determine the data provided to pixels 144A, 144B, 144C, 144D and 144E, respectively. Similarly, the processor 106 utilizes the data received from sensors 111, 113, 115, 117 and 119 to determine the data which is to be provided to pixels 142A, 142B, 142C, 142D and 142E, respectively.

According to the present invention, the right side image and the left side image are detected at the same time and hence, can also be displayed at the same time. According to another aspect of the present invention, each of the light sensors 110, 111, 112, 113, 114, 115, 116, 117, 118, and 119, includes a plurality, of color sensing elements, which together cover a predetermined spectrum, as will be described in detail herein below.

Figure 2:
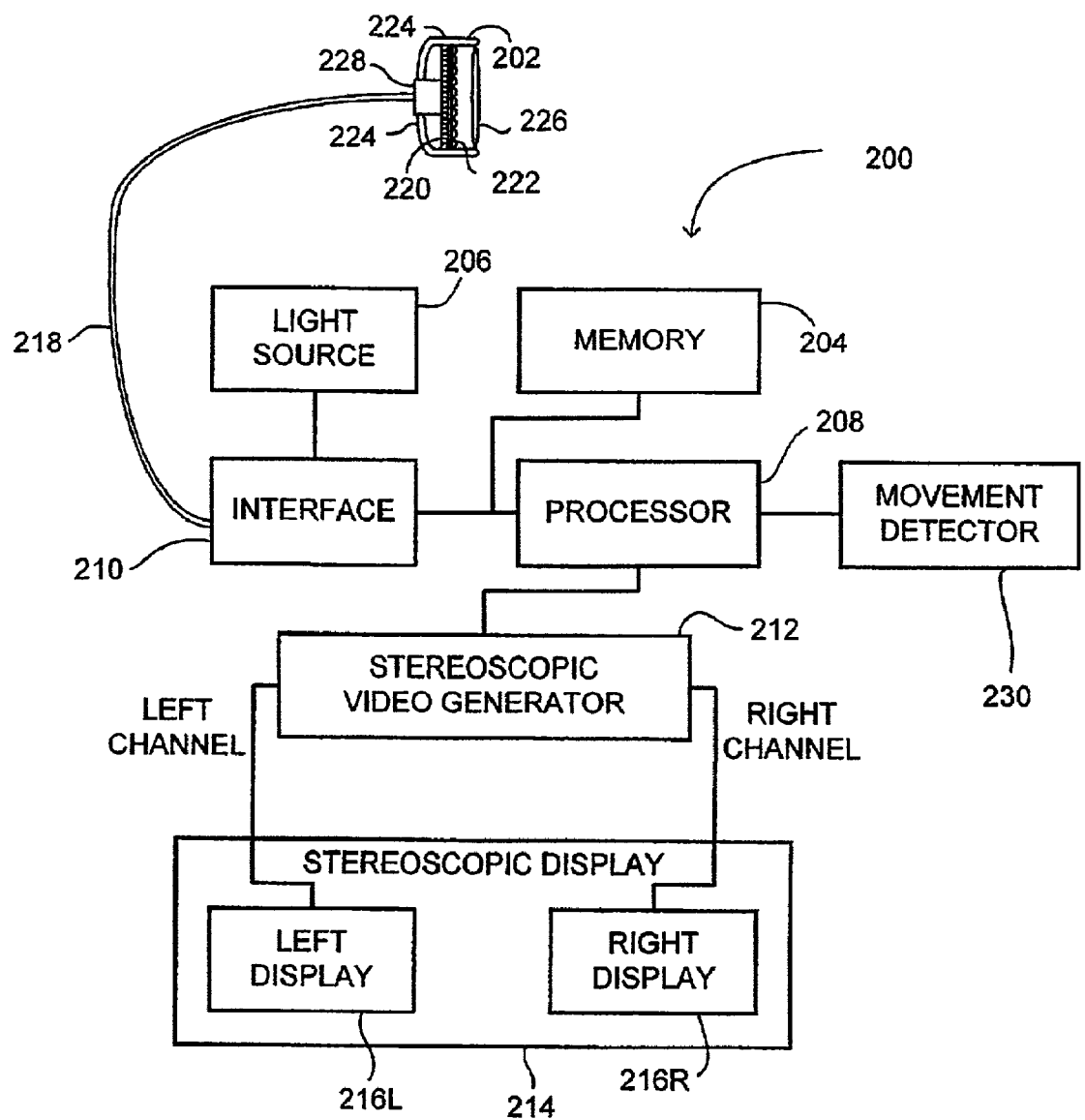
FIG. 2 is a schematic illustration of a stereoscopic vision apparatus, constructed and operative in accordance with another preferred embodiment of the present invention.

Reference is now made to FIG. 2, which is a schematic illustration of a stereoscopic vision apparatus, generally referenced 200, constructed and operative in accordance with another preferred embodiment of the present invention. Apparatus 200 includes a sensor assembly 202, an interface 210, a processor 208, a movement detector 230, a light source 206, a memory unit 204, a stereoscopic video generator 212 and a stereoscopic display 214. The sensor assembly 202 is connected to the interface 210 by a flexible cord 218. The interface 210 is connected to processor 208, memory unit 204, and to light source 206. The processor 208 is further connected to the memory unit 204, movement detector 230 and to the stereoscopic video generator 212. The stereoscopic video generator 212 is further connected to the stereoscopic display 214. Movement detector 230 detects the movement of sensor assembly 202 relative to an object. For this purpose, movement detector 230 is attached to sensor assembly 202. In the case of a rigid endoscope, the movement detector 230 can be attached to any part of the endoscope rod (not shown), since the movement of the endoscope head can be determined according to the movement of any point of the endoscope rod. The operation of system 200, according to data received from movement detector 230, is described herein below.

The sensor assembly 202 includes a focusing element, which in the present example is a lens 226, a lenticular lens layer 222, a light sensor array 220, an interface 228 and a light projecting means 224. The lenticular lens layer 222 is attached to the light sensor array 220. According to the invention, the light sensor array 220 can be any type of sensing array, such as a CCD detector, a CMOS detector, and the like. The light sensor array 220 is connected to the interface 228, which can also acts as a supporting base.

The stereoscopic display 214 includes two display units, a left display unit 216L (for placing in front of the left eye of the user) and a right display unit 216R (for placing in front of the right eye of the user). Hence, the stereoscopic display 214 is capable of displaying stereoscopic images continuously. Such a stereoscopic display unit is for example the ProView 50 ST head-mounted display, manufactured and sold by Kaiser Electro-Optics Inc., a US registered company, located in Carlsbad, Calif. Another example for a stereoscopic display unit is the virtual retinal display (VRD) unit, which is provided by MICROVISION Inc., a US registered company, located in Seattle, Wash. It is noted that any method, which is known in the art for displaying stereoscopic, and for that matter three-dimensional images, is applicable for the present invention.

The image received from a three-dimensional object is received at the sensor assembly 202, focused by lens 226, optically processed by the lenticular lens layer 222 and finally detected by the light sensor array 220. The lenticular lens layer 222 directs light coming from one predetermined direction to predetermined light sensors of the light sensor array 220, and light coming from another predetermined direction to other predetermined light sensors of the light sensor array 220. Accordingly, light sensor array 220 detects two images of the same object, a right side image and a left side image, each from a different direction. This aspect of the invention is described in detail hereinabove, in conjunction with FIG. 1.

An electronic representation of this information is partially processed by the interface 228 and then provided to the interface 210, via flexible cord 218. It is noted that flexible cord 218 includes digital communication linking means such as optic fibers or electrical wires, for transferring data received from light sensor array 220, as well as light guiding conducting means for conducting light from light source 206 to the light projecting means 224. According to the present invention, flexible cord 218 can be replaced with a rigid cord (not shown), if necessary.

The data received at interface 210 includes information, which relates to the two images and has to be processed so as to distinguish them from each other. As the processor 208 processes the information, it uses the memory unit 204 as temporarily storage.

After processing the information, the processor 208 produces two matrices each being a reconstructed representation relating to one of the originally detected images. The processor provides these matrixes to the stereoscopic video generator 212, which in turn produces two respective video signals, one for the left view image and another for the right view image.

The stereoscopic video generator 212 provides the video signals to the stereoscopic display 214, which in turn produces two images, one using right display unit 216R and another using left display unit 216L.

It is noted that the general size of the sensor assembly 202 is dictated by the size of the sensor array and can be in the order of a few millimeters or a few centimeters. This depends on the size of each of the sensors in the array and the total number of sensors (i.e. the required optical resolution).

According to one aspect of the invention, each of the sensors in light sensor array 220, is a full range sensor, which yields data relating to a gray scale stereoscopic image. According to another aspect of the invention, each of the sensors in the light sensor array, can be adapted so as to provide full color detection capabilities.

Figure 3A:
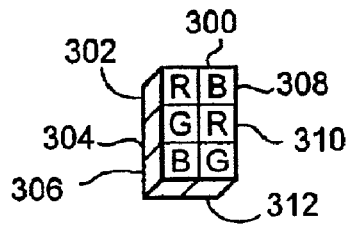
FIG. 3A is a schematic illustration of a super-pixel, constructed and operative in accordance with a further preferred embodiment of the present invention.

Reference is now made to FIG. 3A, which is a schematic illustration of a super-pixel, generally referenced 300, constructed and operative in accordance with a further preferred embodiment of the present invention. Super-pixel 300 includes a left section of sensors which includes three sensors 302, 304 and 306, and a right section of sensors which also includes three sensors 308, 310 and 312. Sensors 302 and 310 detect generally red colored light, sensors 304 and 312 detect generally green colored light and sensors 306 and 308 detect generally blue colored light. Hence, each of the sections includes a complete set of sensors for detecting light in the entire visible spectrum.

Figure 3B:
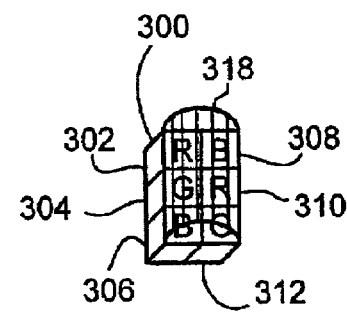
FIG. 3B is a schematic illustration of the super-pixel of FIG. 3A and a lenticular element, constructed and operative in accordance with a another preferred embodiment of the present invention.

Reference is further made to FIG. 3B, which is a schematic illustration of the super-pixel 300 of FIG. 3A and a lenticular element, generally referenced 318, constructed and operative in accordance with another preferred embodiment of the present invention. The lenticular element 318 is located on top of super-pixel 300, where its right side covers the right section of the super-pixel 300, and its left side covers the left section of the super-pixel 300. Accordingly, the lenticular element 318 directs light, which arrives from the right (right view image), to the left section of the super-pixel 300, where it is detected in full spectrum by sensors 302, 304 and 306.

The data provided by these sensors can later be utilized to reconstruct an image in full color. Similarly, the lenticular element 318 directs light, which arrives from the left (left view image), to the right section of the super-pixel 300, where it is detected in full spectrum by sensors 308, 310 and 312.

Figure 3C:
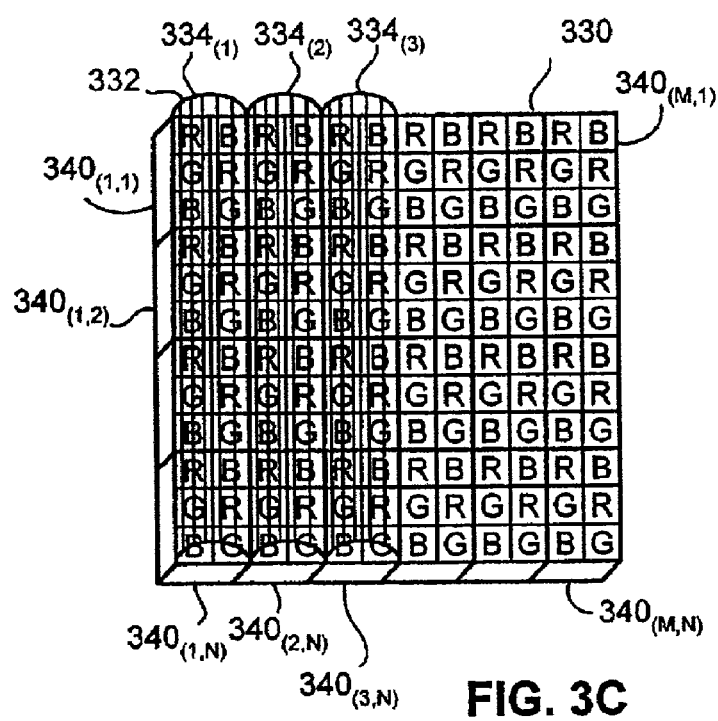
FIG. 3C is a schematic illustration of a sensor array and a lenticular lens layer, constructed and operative in accordance with a further preferred embodiment of the present invention.

Reference is now made to FIG. 3C, which is a schematic illustration of a sensor array, generally referenced 330, and a lenticular lens layer, generally referenced 332, constructed and operative in accordance with a further preferred embodiment of the present invention. Sensor array 330 is a matrix of M×N super-pixels, which are generally referenced 340. For example, the upper left super-pixel is denoted $340_{(1,1)}$, the last super-pixel in the same column is denoted $340_{(1,N)}$ and the lower-right pixel is denoted $340_{(M,N)}$. A lenticular lens layer 332 of which three lenticular elements are shown (referenced 334), is placed over the sensor array 330.

Lenticular element $334_{(1)}$ covers the first column of super-pixels 340 from super-pixel $340_{(1,1)}$ to super-pixel $340_{(1,N)}$. Lenticular element $334_{(2)}$ covers the second column of super-pixels 340 from super-pixel $340_{(2,1)}$ to super-pixel $340_{(2,N)}$. Lenticular element 334(3) covers the third column of super-pixels 340 from super-pixel $340_{(3,1)}$ to super-pixel $340_{(3,N)}$. Accordingly, each of the lenticular elements of the lenticular lens layer covers an entire column of super-pixels.

It is noted that a super-pixel according to the present invention can include sensors in any set of colors such as red-green-blue (RGB), cyan-yellow-magenta-green (CYMG), infra-red, ultra-violet, and the like, in any arrangement or scheme such as columns, diagonals, and the like. It is noted that such a set of colors can be achieved either by using specific color sensitive detectors or by using color filters over the wide spectrum detectors.

Figure 4:
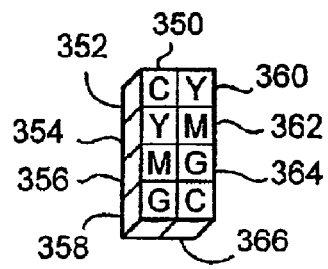
FIG. 4 is a schematic illustration of a super-pixel, constructed and operative in accordance with another preferred embodiment of the present invention.

Reference is further made to FIG. 4, which is a schematic illustration of a super-pixel, generally referenced 350, constructed and operative in accordance with another preferred embodiment of the present invention. Super-pixel 350 includes a left section of sensors which includes four sensors 352, 354, 356 and 358 and a right section of sensors which also includes four sensors 360, 362, 364 and 366. Sensors 352 and 366 detect generally cyan colored light, sensors 354 and 360 detect generally yellow colored light, sensors 356 and 362 detect generally magenta colored light and sensors 358 and 364 detect generally green colored light. Hence, each of the sections includes a complete set of sensors for detecting light in the entire visible spectrum.

Figure 5A:
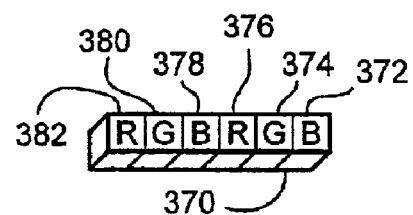
FIG. 5A is a schematic illustration of a color super-pixel, constructed and operative in accordance with a further preferred embodiment of the present invention.
Figure 5B:
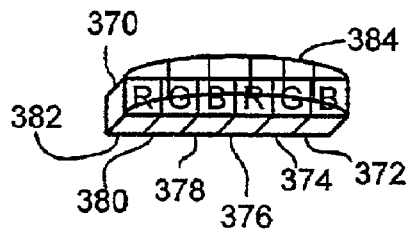
FIG. 5B is a schematic illustration of the color super-pixel of FIG. 5A, with a single lenticular element, constructed and operative in accordance with another preferred embodiment of the present invention.
Figure 5C:
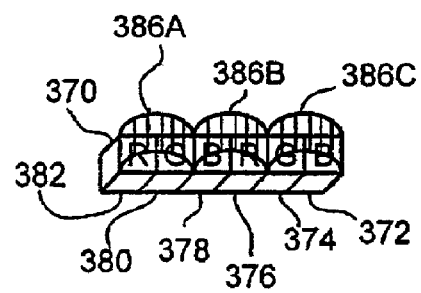
FIG. 5C is a schematic illustration of the color super-pixel of FIG. 5A, combined with three lenticular elements, constructed and operative in accordance with a further preferred embodiment of the present invention.

Reference is further made to FIGS. 5A, 5B and 5C. FIG. 5A is a schematic illustration of a super-pixel, generally referenced 370, constructed and operative in accordance with a further preferred embodiment of the present invention. FIG. 5B is a schematic illustration of super-pixel 370 combined with a single lenticular element, generally referenced 384, constructed and operative in accordance with another preferred embodiment of the present invention. FIG. 5C is a schematic illustration of super-pixel 370 combined with three lenticular elements, generally referenced 386, constructed and operative in accordance with a further preferred embodiment of the present invention.

The color arrangement which is provided for super-pixel 370 is typical for vertical light detection arrays, where each column of sensors is coated with light filtering layer of a different color. As can be seen in FIG. 5A, super-pixel 370 includes a plurality of light sensors 372, 374, 376, 378, 380 and 382. Light sensors 372 and 378 are blue color range sensors. Light sensors 374 and 380 are green color range sensors. Light sensors 376 and 382 are red color range sensors.

Figure 6:
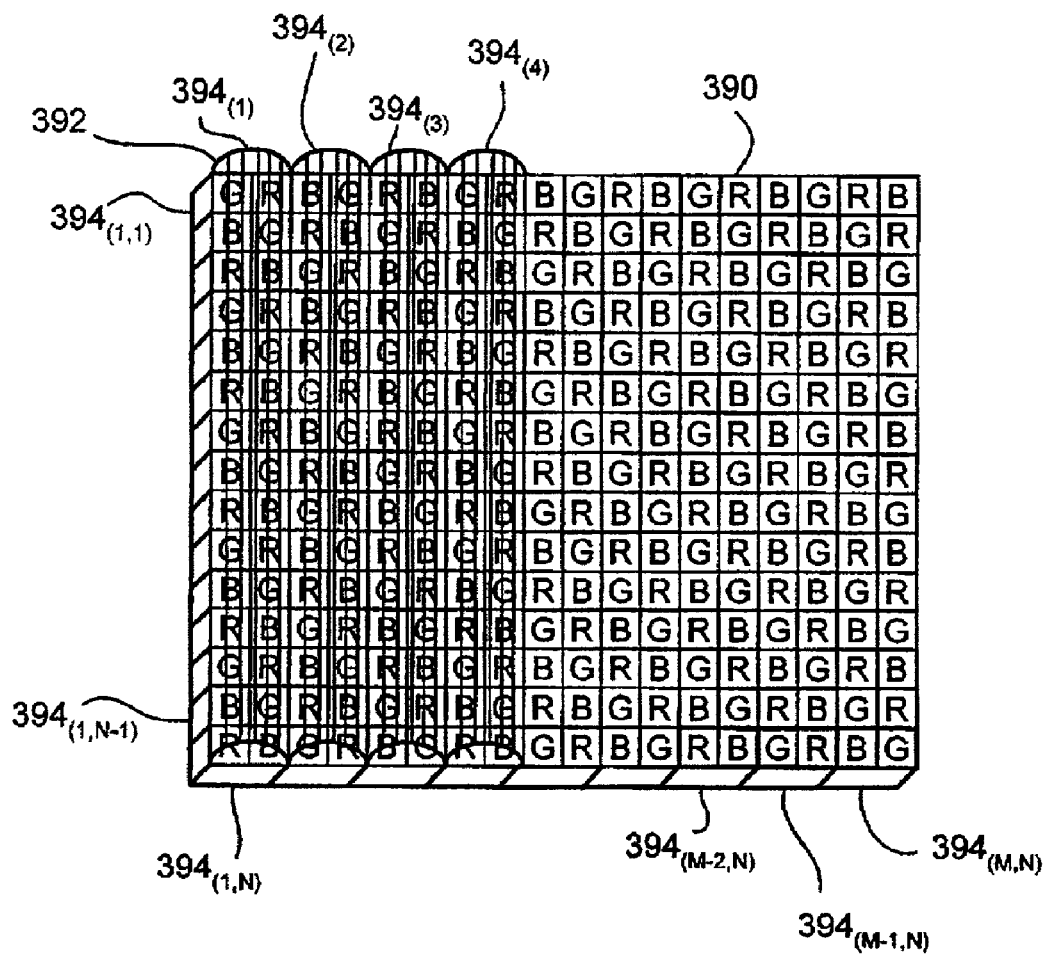
FIG. 6 is a schematic illustration of a sensor array and a lenticular lens layer, constructed and operative in accordance with another preferred embodiment of the present invention.

Reference is now made to FIG. 6, which is a schematic illustration of a sensor, generally referenced 390, and a lenticular lens layer, generally referenced 392, constructed and operative in accordance with another preferred embodiment of the present invention. Sensor 390 is logically divided into a plurality of super-pixels, generally referenced $394_{(x,y)}$. For example, the upper-left super-pixel is referenced $394_{(1,1)}$ and the lower-right side super-pixel is referenced $394_{(M,N)}$.

As can be seen from FIG. 6, the color arrangement of sensor 390 is diagonal. Hence, each super pixel has a different color arrangement, and generally speaking, there are several types of super-pixels, such as red-blue (super pixel $394_{(M-2,N)}$), green-red (super pixel $394_{(M-1,N)}$) and blue-green (super pixel $394_{(M,N)}$).

Figure 7A:
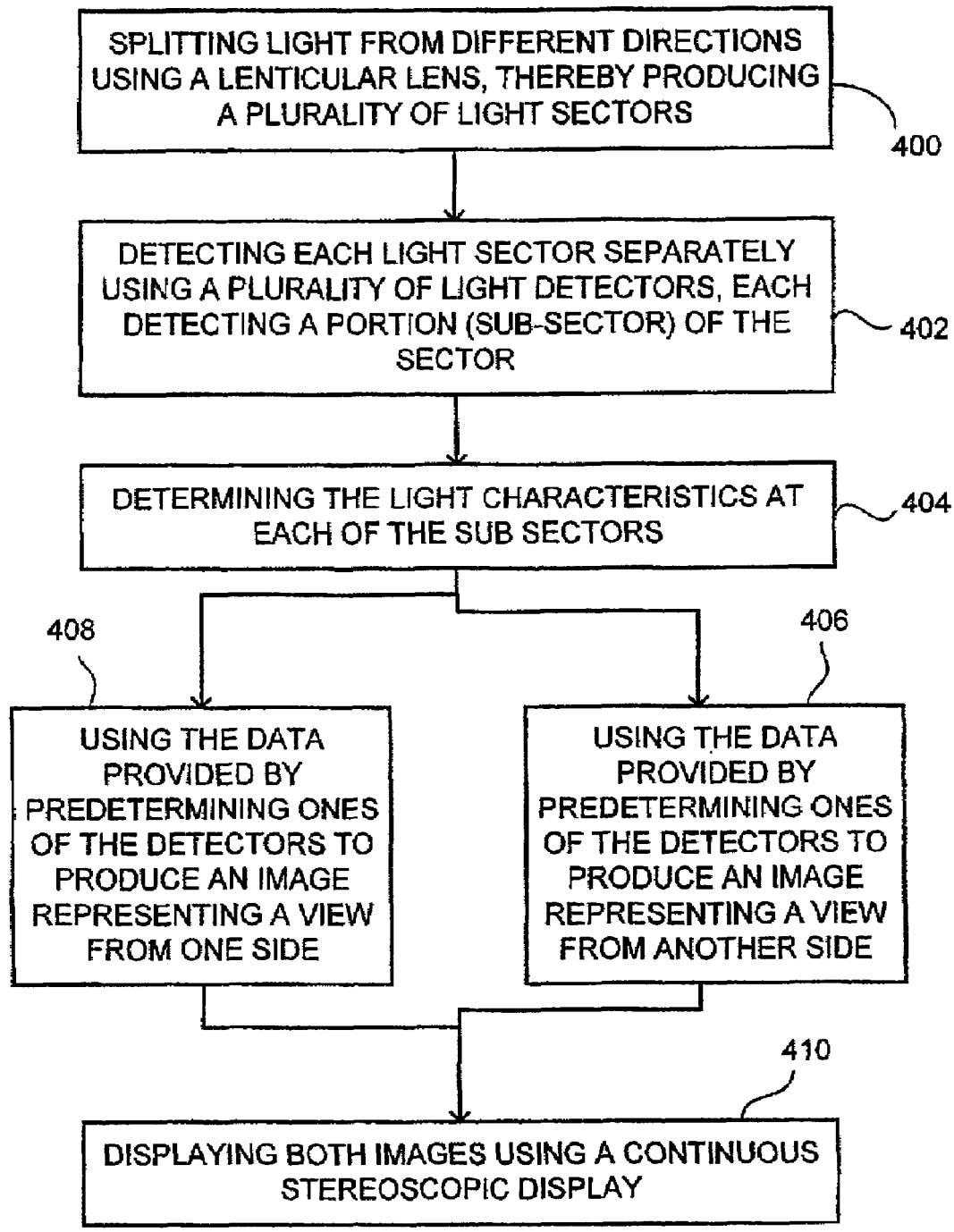
FIG. 7A is a schematic illustration of a method for operating the apparatus of FIG. 2, operative in accordance with a further preferred embodiment of the present invention.

Reference is now made to FIG. 7A, which is a schematic illustration of a method for operating apparatus 200, operative in accordance with a further preferred embodiment of the present invention. In step 400, the apparatus 200 splits light which arrives from different directions, utilizing the lenticular lens 222. Each of the lenticular elements produces two light sectors, one sector which includes light rays arriving from the left side, and another sector which includes light rays arriving from the right side.

In step 402, the apparatus detects each light sector separately, using a plurality of light detectors, each detecting a portion of its respective sector. With reference to FIG. 3B, sensors 302, 304 and 306 detect light which arrives from the lenticular element 318, at the left side sector and sensors 308, 310 and 312 detect light which arrives from the lenticular element 318, at the right side sector. Each of the sensors detects light at a sub-sector.

In step 404, the apparatus 200 determines the light characteristics as detected by each of the light sensors, at each of the sub-sectors. In step 408, the apparatus 200 utilizes the data, which was accumulated from selected sub-sectors to determine and produce an image representing a view from one side. In step 406, the apparatus 200 utilizes the data, which was accumulated from other selected sub-sectors to determine and produce an image representing a view from another side. In step 410, the apparatus 200 displays both images using a continuous stereoscopic display device.

According to a further aspect of the invention, information from selected pixels can be used to enhance information for other pixels. For example, color information of pixels, which are associated with a first color, is used for extrapolating that color at the location of another pixel, associated with a second color.

Figure 7B:
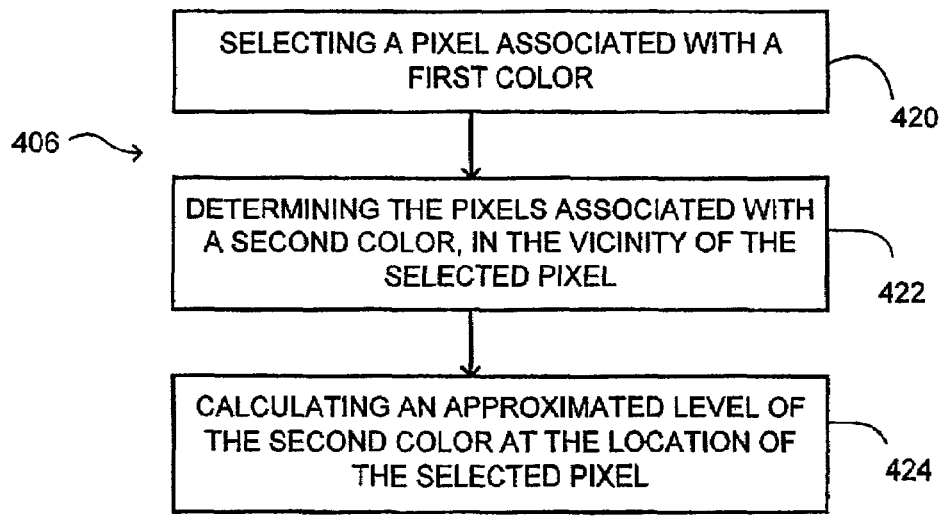
FIG. 7B is an illustration in detail of a step of the method of FIG. 7A.
Figure 7C:
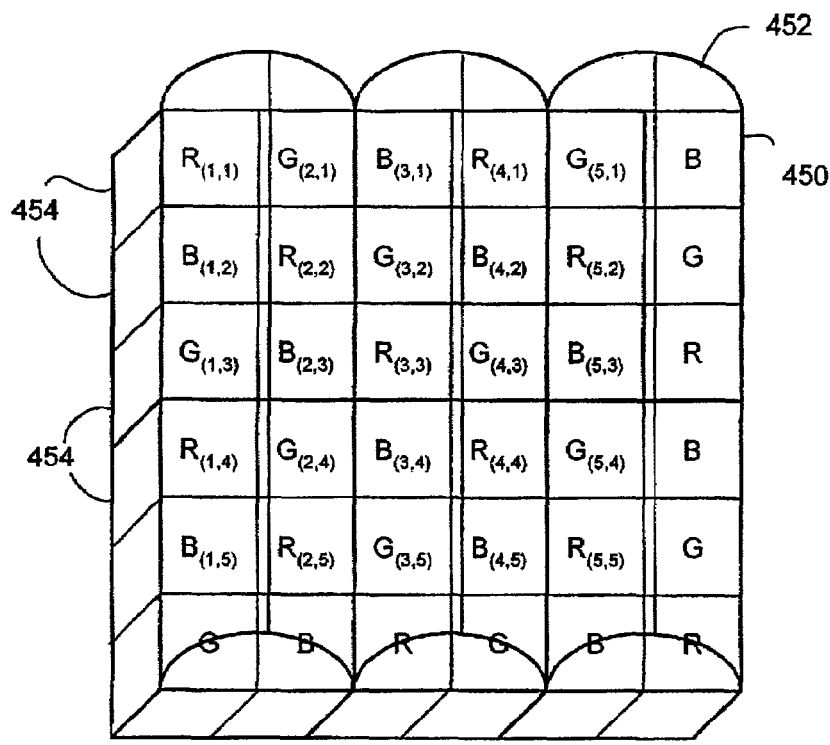
FIG. 7C is a schematic illustration of a sensor array and a lenticular lens layer, constructed and operative in accordance with another preferred embodiment of the present invention.

Reference is further made to FIGS. 7B and 7C. FIG. 7B is an illustration in detail of step 406 of FIG. 7A. FIG. 7C is a schematic illustration of a sensor array, generally referenced 450, and a lenticular lens layer, generally referenced 452, constructed and operative in accordance with another preferred embodiment of the present invention. Sensor array 450 includes a plurality of pixel sensors, referenced 454, each associated with a selected color. For example, pixel sensors $R_{(1,1)}$, $R_{(2,2)}$, $R_{(3,3)}$, $R_{(4,4)}$, $R_{(1,4)}$ and $R_{(4,1)}$ are associated with the red color. Pixel sensors $G_{(2,1)}$, $G_{(3,2)}$, $G_{(4,3)}$, $G_{(1,3)}$ and $G_{(2,4)}$ are associated with the green color. Pixel sensors $B_{(1,2)}$, $B_{(2,3)}$, $B_{(3,4)}$, $B_{(3,1)}$ and $B_{(4,2)}$ are associated with the blue color.

In step 420, the system, according to the invention, selects a pixel sensor, associated with a first color. With reference to FIG. 7C, the selected pixel sensor according to the present example is pixel sensor $R_{(3,3)}$.

In step 422, the system determines pixels, associated with a second color, in the vicinity of the selected pixel. It is noted that these pixels can also be restricted to ones, which relate to the same image side of the selected pixel. With reference to FIG. 7C, the second color is green and the green pixel sensors, in the vicinity of pixel sensor $R_{(3,3)}$, respective of the same image side are pixel sensors $G_{(5,1)}$, $G_{(3,2)}$, $G_{(3,5)}$, $G_{(5,4)}$, and $G_{(1,3)}$.

In step 424, the system calculates an approximation of the level of the green color at the location of the selected pixel $R_{(3,3)}$. It is noted that the calculation can include a plurality of approximation procedures, such as calculating the weighted average level, depending on the location of pixel sensors $G_{(5,1)}$, $G_{(3,2)}$, $G_{(3,5)}$, $G_{(5,4)}$, and $G_{(1,3)}$, with respect to the location of the selected pixel sensor $R_{(3,3)}$. Similarly, blue color level at the location of the selected pixel sensor $R_{(3,3)}$, can be calculated using the information received from pixel sensors $B_{(1,2)}$, $B_{(1,5)}$, $B_{(3,1)}$, $B_{(3,4)}$ and $B_{(5,3)}$. Hence the present invention provides a method for enhancing picture resolution by means of color information interpolation, using image processing.

It is noted that none of the lenticular elements is necessarily round shaped, but can be formed according to other optical structures which are based on various prism designs, and the like, which provide the directing of beams of light coming from different directions to different directions.

Figure 8:
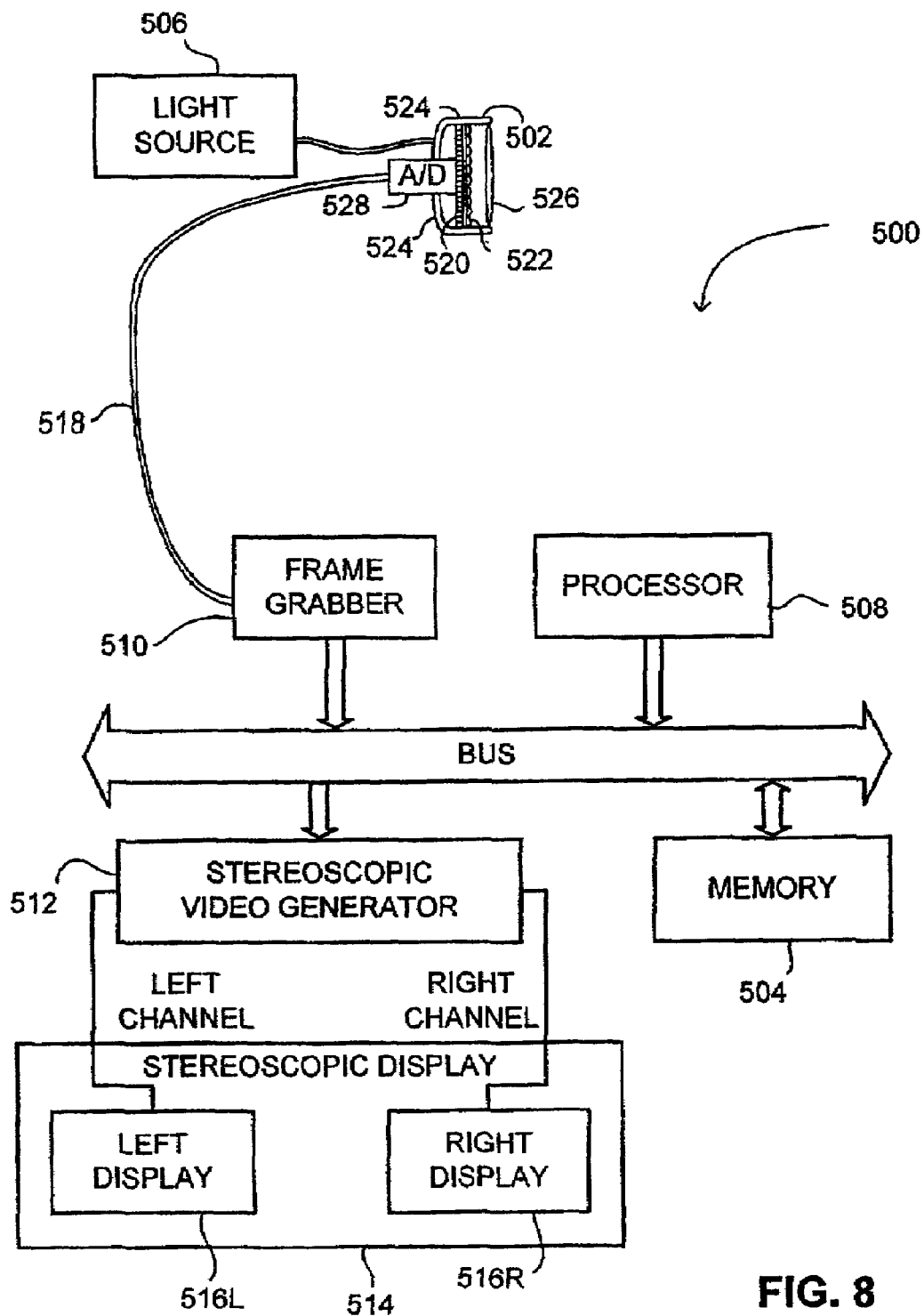
FIG. 8 is a schematic illustration of a stereoscopic vision apparatus, constructed and operative in accordance with a further preferred embodiment of the present invention.

Reference is now made to FIG. 8, which is a schematic illustration of a stereoscopic vision apparatus, generally referenced 500, constructed and operative in accordance with a further preferred embodiment of the present invention. Apparatus 500 includes a sensor assembly 502, a frame grabber 510, a processor 508, a light source 506, a memory unit 504, a stereoscopic video generator 512 and a stereoscopic display 514. The sensor assembly 502 is connected to the frame grabber 510 by a flexible cord 518. The frame grabber 510, the processor 508, the memory unit 504 and the stereoscopic video generator 512 are all interconnected via a common bus.

The sensor assembly 502 is generally similar to the sensor assembly 202, as described herein above in conjunction with FIG. 2. The sensor assembly 502 includes a lens 526, a lenticular lens layer 522, a light sensor array 520, an analog to digital converter (A/D) 528 and a light projecting means 524. The lenticular lens layer 522 is attached to the light sensor array 520. Light sensor array 520 is connected to the A/D 528, which could also act as a supporting base. The light projecting means 524 is connected to light source 506, which provides light thereto.

The stereoscopic display 514 includes two display units, a left display unit 516L (for placing in front of the left eye of the user), and a right display unit 516R (for placing in front of the right eye of the user). Hence, the stereoscopic display 514 is capable of displaying stereoscopic images continuously. A/D converter 528 converts analog information received from light sensor array 522 into digital format and provides the digital information to frame grabber 510.

The digital information is received by the frame grabber 510 and hence made available to the processor 508 via the bus. As the processor 508 processes the information, it uses the memory unit 504 as temporary storage. After processing the information, the processor 508 produces two matrices each being a reconstructed representation relating to one of the originally detected images. The processor 508 provides these matrices to the stereoscopic video generator 512, which in turn produces two respective video signals, one for the left view image and another for the right view image. The stereoscopic video generator 512 provides the video signals to the stereoscopic display 514, which in turn produces two images, one using right display unit 516R and another using left display unit 516L.

Figure 9A:
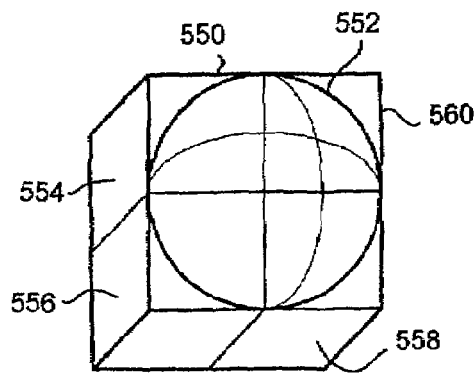
FIG. 9A is a view in perspective of a section of light sensors, and a lenticular element, constructed and operative in accordance with another preferred embodiment of the present invention.
Figure 9B:
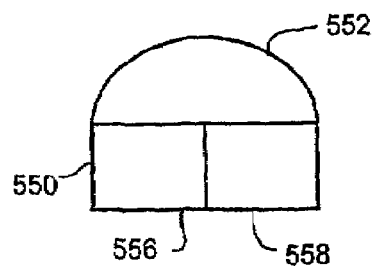
FIG. 9B is a view from the bottom of the lenticular element and the section of light sensors of FIG. 9A.
Figure 9C:
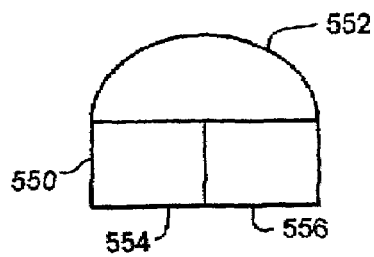
FIG. 9C is a view from the side of the lenticular element and the section of light sensors of FIG. 9A.

Reference is now made to FIGS. 9A, 9B and 9C. FIG. 9A is a view in perspective of a super-pixel, generally referenced 550, and a lenticular element, generally referenced 552, constructed and operative in accordance with another preferred embodiment of the present invention. FIG. 9B is a view from the bottom of the lenticular element 552 and the super-pixel 550 of FIG. 9A. FIG. 9C is a view from the side of the lenticular element 552 and the super-pixel 550 of FIG. 9A.

The super-pixel 550 includes four sensor sections, 554, 556, 558 and 560, arranged in a rectangular formation. The lenticular element 552 is shaped like a dome and is basically divided into four sections, each facing a different one of the sensor sections 554, 556, 558 and 560.

The super-pixel 550 and the lenticular element 552 form together, an optical detection unit, which is capable of detecting and distinguishing light which arrives from four different directions. The lenticular element 552 directs a portion of the upper-left side view of the detected object to sensor section 554 and directs a portion of the lower-left side view of the detected object to sensor section 556. In addition, the lenticular element 552 directs a portion of the upper-right side view of the detected object to sensor section 560 and a portion of the lower-right side view of the detected object to sensor section 558.

It is noted that according to a further aspect of the invention, the four-direction arrangement, which is described in FIGS. 9A, 9B and 9C can be used to logically rotate the image which is provided to the user, without physically rotating the device itself. At first, sensor sections 560 and 558 are used to form the right-side image and sensor sections 554 and 556 are used to form the left-side image. A rotation at an angle of 90° clockwise, is provided by assigning sensor sections 554 and 560, to form the right side image, and assigning sensor sections 556 and 558, to form the left-side image. It is further noted that a rotation in any desired angle can also be performed by means of a linear or other combination of sensor sections when reconstructing the final images.

Figure 10:
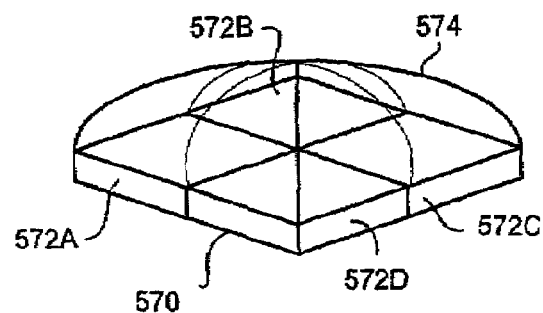
FIG. 10 is a view in perspective of a section of light sensors, and a lenticular element, constructed and operative in accordance with a further preferred embodiment of the present invention.

Reference is now made to FIG. 10, which is a view in perspective of a section of light sensors, generally referenced 570, and a lenticular element, generally referenced 572, constructed and operative in accordance with a further preferred embodiment of the present invention. Lenticular element 572 is extended to cover the entire area of the section of pixels, so as to enhance light transmission thereto.

Figure 11:
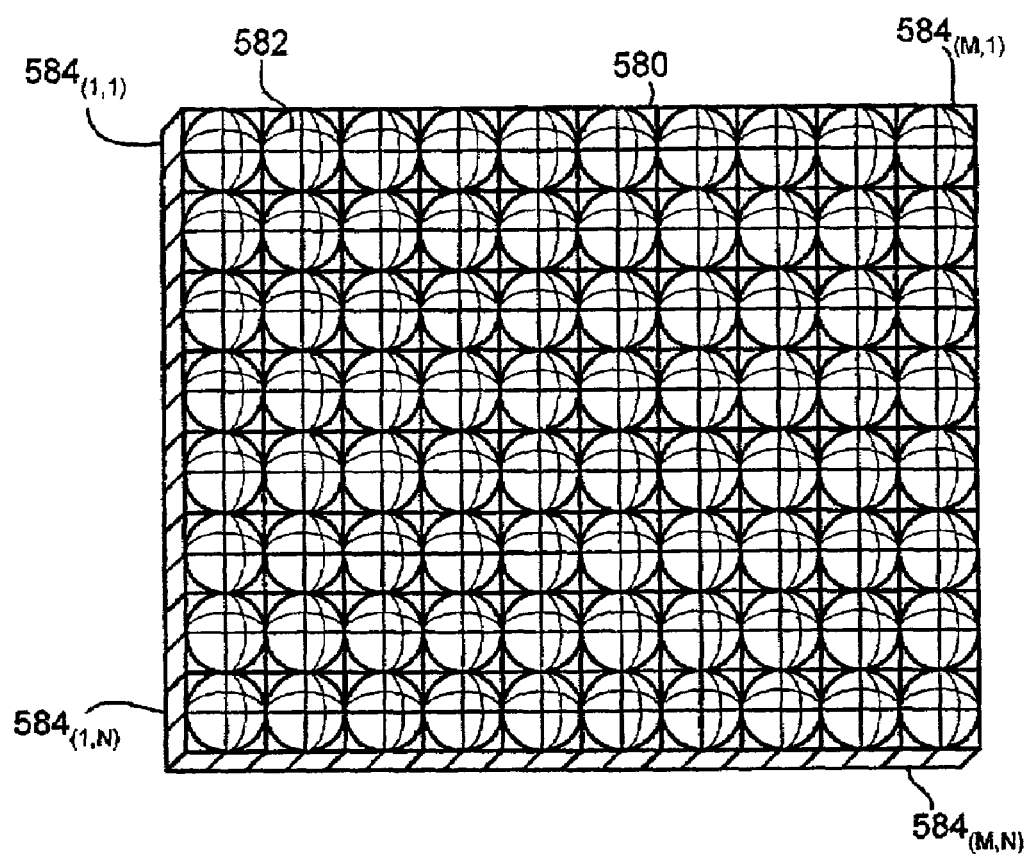
FIG. 11 is a view in perspective of a sensor array and a lenticular lens layer, constructed and operative in accordance with another preferred embodiment of the present invention.

Reference is now made to FIG. 11, which is a view in perspective of a sensor array, generally referenced 580, and a lenticular lens layer, generally referenced 582, constructed and operative in accordance with another preferred embodiment of the present invention. The lenticular lens layer 582 includes a plurality of four direction lenticular elements such as described in FIGS. 9A and 10. The sensor array 580 is logically divided into a plurality of sensor sections, generally referenced $584_{(x,y)}$. For example, the upper left sensor section is referenced $584_{(1,1)}$ and the lower-right sensor section is referenced $584_{(M,N)}$. Each of the sensor sections is located beneath a lenticular element and detects light directed thereby.

Figure 12A:
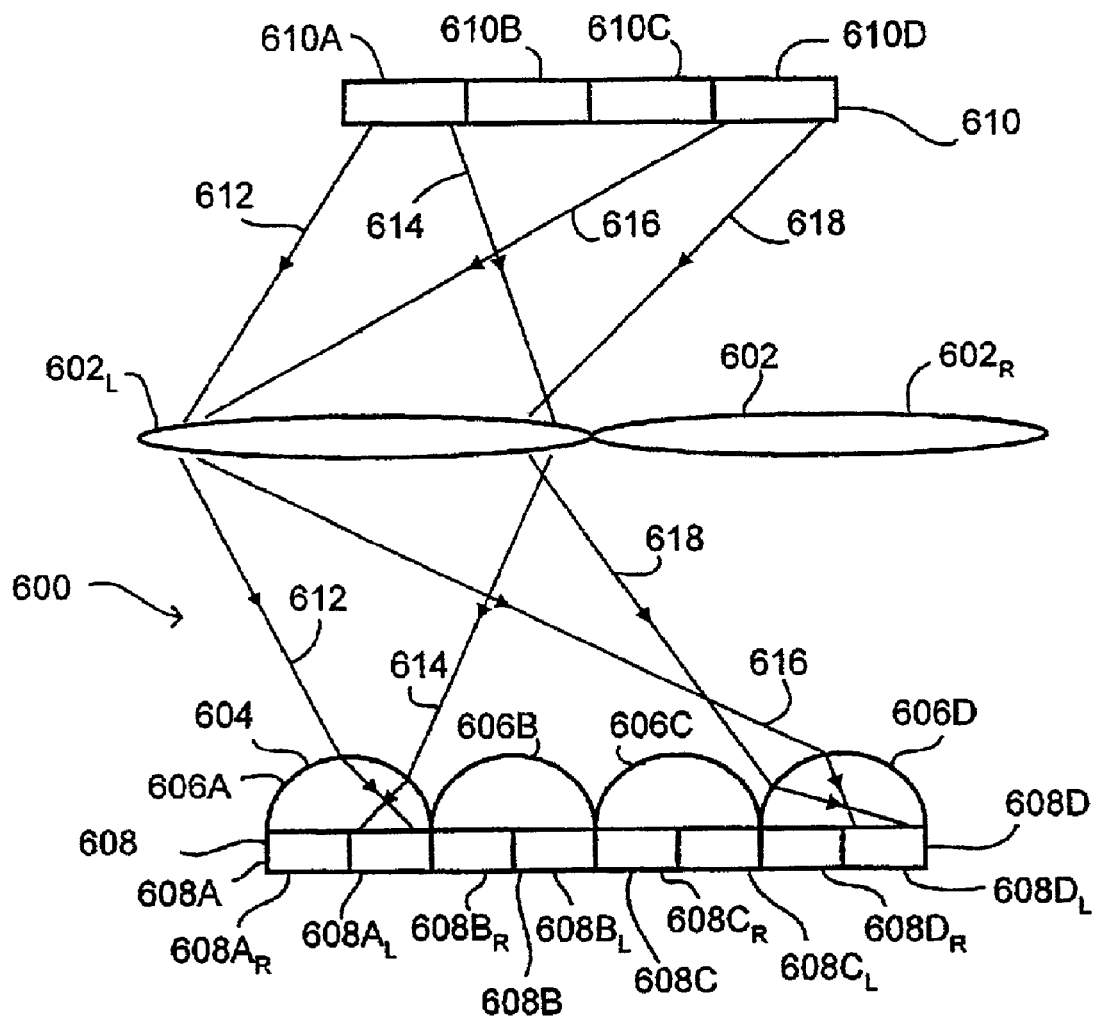
FIG. 12A is a schematic illustration of a detection apparatus, constructed and operative in accordance with a further preferred embodiment of the present invention.
Figure 12B:
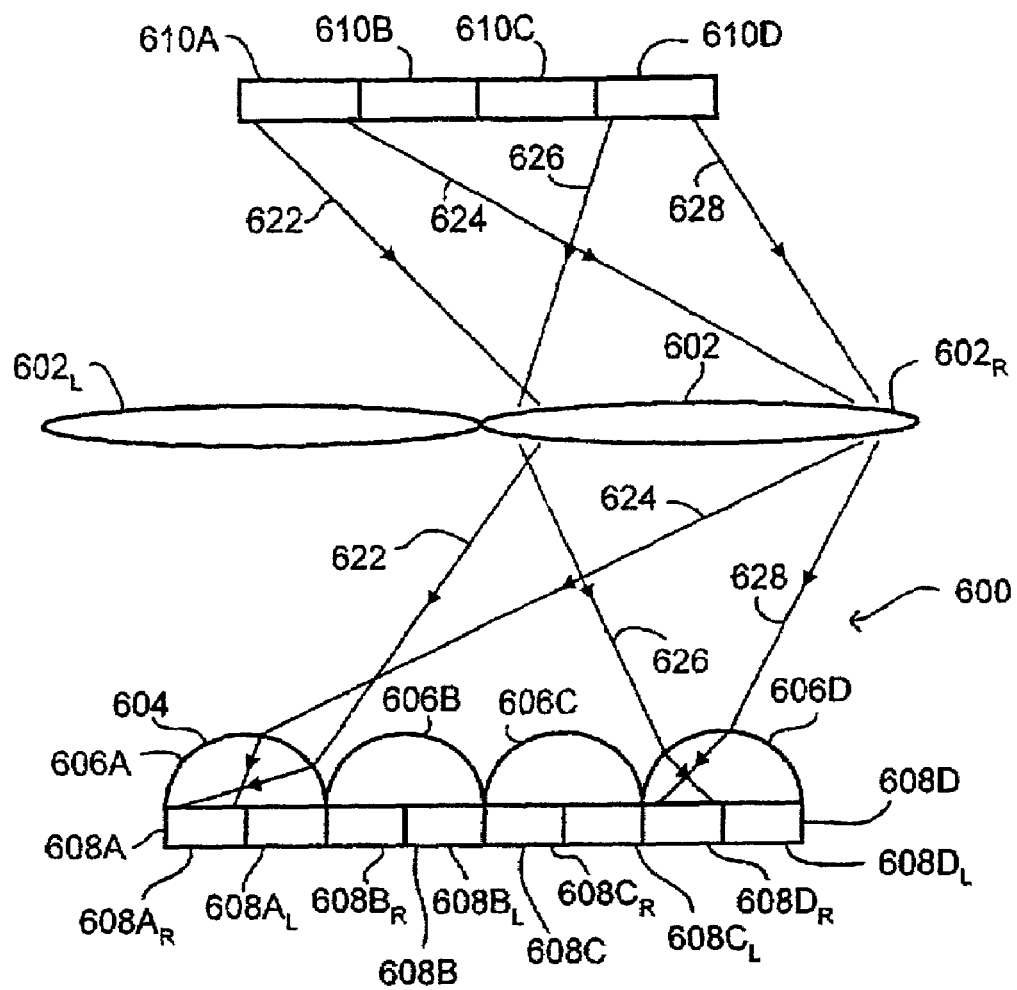
FIG. 12B is another schematic illustration of the detection apparatus of FIG. 12A.

Reference is now made to FIGS. 12A and 12B. FIG. 12A is a schematic illustration of a detection apparatus, generally referenced 600, constructed and operative in accordance with a further preferred embodiment of the present invention. FIG. 12B is another schematic illustration of detection apparatus 600, of FIG. 12A.

Detection apparatus 600 includes an optical assembly 602, a lenticular lens layer 604 and an array of sensors 608. The detection apparatus 600 detects images of an object 610, which includes a plurality of object sections 610A, 610B, 610C and 610D.

Sensor array 608 includes a plurality of super-pixels 608A, 608B, 608C and 608D. Each of these super-pixels is divided into a left-side section and a right-side section. For example, super-pixel 608A includes a left-side section, designated $608A_L$ and a right-side section, designated $606A_R$.

The optical assembly 602 is divided into two optical sections $602_L$ and $602_R$, each directed at transferring an image, which represents a different side view. Optical section $602_R$ transfers an image, which is a view from the right side of object 610. Optical section $602_L$ transfers an image, which is a view from the left side of object 610.

A plurality of light rays 612, 614, 616 and 618 are directed from all sections of the object 610 to the left side of optical assembly 602 (i.e., optical section $602_L$), and are directed to the lenticular lens layer 604. Here, these rays are further directed to the left-side view associated sensor sections, which are sensor sections $608_L$ (i.e., sensor sections $608A_L$, $608B_L$, $608C_L$ and $608D_L$).

With reference to FIG. 12B, a plurality of light rays 622, 624, 626 and 628 are directed from all sections of the object 610 to the right side of optical assembly 602 (i.e., optical section $602_R$), and are directed to the lenticular lens layer 604. Here, these rays are further directed to the right-side view associated sensor sections, which are sensor sections $608A_R$, $608B_R$, $608C_R$ and $608D_R$.

Figure 13:
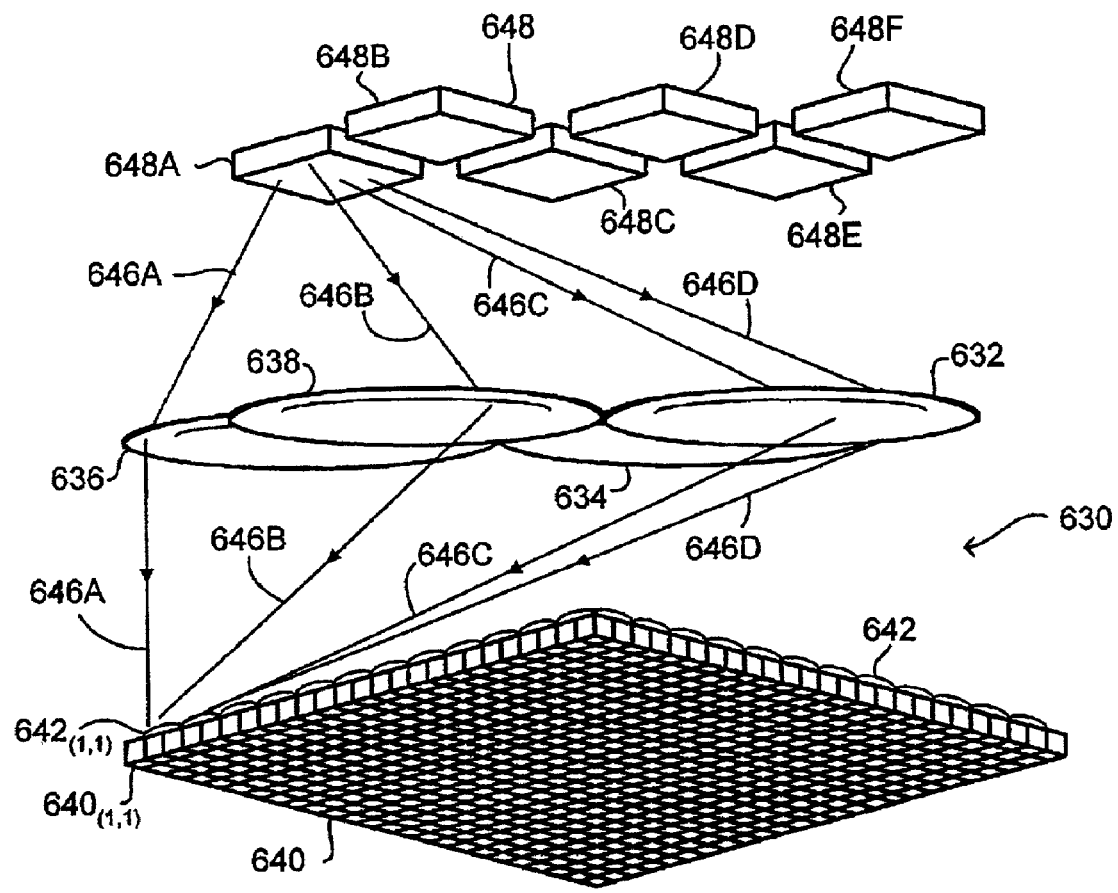
FIG. 13 is a schematic illustration of a detection apparatus, constructed and operative in accordance with another preferred embodiment of the present invention.

Reference is now made to FIG. 13, which is a schematic illustration of a detection apparatus, generally referenced 630, constructed and operative in accordance with another preferred embodiment of the present invention. Detection apparatus 630 includes an optical assembly, which is divided into four sections 632, 634, 636 and 638, a lenticular lens layer 642 and an array of sensors 640. The detection apparatus 630 detects images of an object 648, which includes a plurality of object sections 648A, 648B, 648C, 648D, 648E and 648F. Light rays, which arrive from object 648 to any of the optical sections, are directed to a lenticular element of the lenticular lens layer 642, according to their origin.

In the present example, all of the light rays 646A, 646B, 646C and 646D arrive from object element 648A. Each of these rays is received at a different optical section. Ray 646A is received and directed by optical section 636, ray 646B is received and directed by optical section 638, ray 646C is received and directed by optical section 634 and ray 646D is received and directed by optical section 632. Each of the optical sections directs its respective ray to a specific lenticular element $642_{(1,1)}$, at the right side of the lenticular lens layer 642. The location of lenticular element $642_{(1,1)}$ is respective of the location of the object element 648A. The lenticular element $642_{(1,1)}$ directs each of the rays to predetermined light sensors within its respective super-pixel $640_{(1,1)}$.

In accordance with a further aspect of the present invention, there is provided a reduced size color stereovision detection system, which uses time-multiplexed colored light projections, and respective time-multiplexed frame grabbing.

Figure 14A:
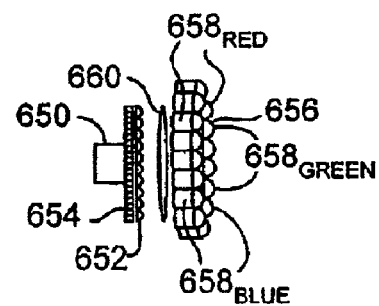
FIG. 14A is a partially schematic partially perspective illustration of a combined illumination and detection device, constructed and operative in accordance with a further preferred embodiment of the present invention.
Figure 14B:
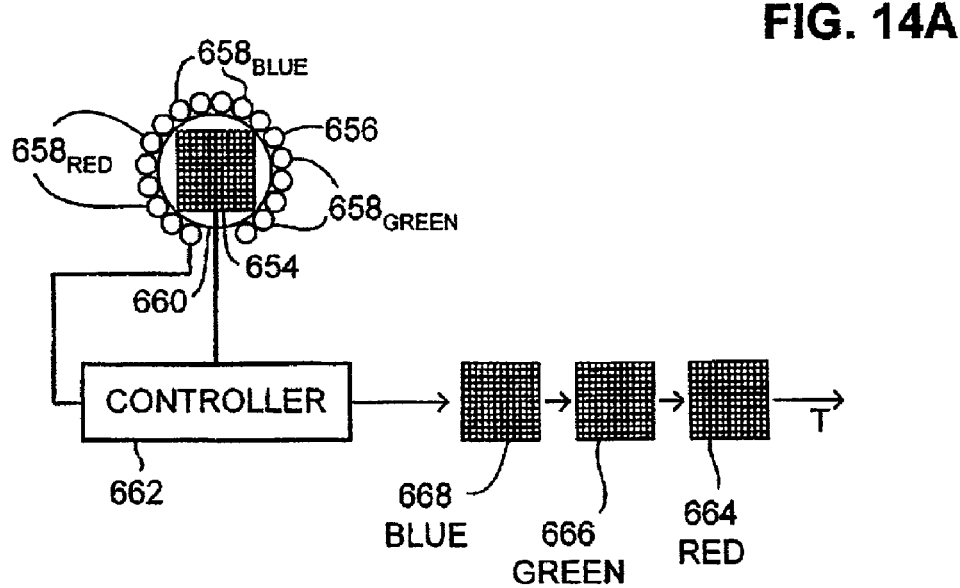
FIG. 14B is a partially schematic partially perspective illustration of the combined illumination and detection device of FIG. 14A, a controller and output frames, constructed and operative in accordance with another preferred embodiment of the present invention.

Reference is now made to FIGS. 14A and 14B. FIG. 14A is a partially schematic, partially perspective illustration of a combined illumination and detection device, generally referenced 650, constructed and operative in accordance with a further preferred embodiment of the present invention. FIG. 14B is a partially schematic, partially perspective illustration of the combined illumination and detection device 650 of FIG. 14A, a controller, generally designated 662, and output frames, constructed and operative in accordance with another preferred embodiment of the present invention.

Device 650 includes a lenticular lens layer 652, a full spectrum sensor array 654, an optical assembly 660 and an illuminating unit 656, surrounding the optical assembly 660. Illuminating unit 656 includes a plurality of illuminating elements, generally referenced 658, each being of a specific predetermined color. Illuminating elements $658_{RED}$ produce generally red light, illuminating elements $658_{GREEN}$ produce generally green light and illuminating elements $658_{BLUE}$ produce generally blue light. It is noted that each of the illuminating elements can be of a specific color (i.e., a specific wavelength), a range of colors (i.e., a range of wavelengths) or alternating colors, for example, a multi-color light emitting diode (LED).

Each group of illuminating elements, which are of the same color, is activated at a different point in time. For example, illuminating elements $658_{RED}$ are activated and shut down first, illuminating elements $658_{GREEN}$ are activated and shut down second and illuminating elements $658_{BLUE}$ are activated and shut down last. Then the illuminating sequence is repeated.

With reference to FIG. 14B, the controller 662 is connected to the sensor array 654 and to the illuminating unit 656. The sensor array 654 includes full spectrum sensors, which are capable of detecting red, green and blue light, but cannot indicate the wavelength of the detected light. The controller 662 associates the images, which are detected at any particular moment, using the sensor array 654, with the color of the illuminating elements, which were active at that particular moment.

Hence, the first detected frame 664 in an illumination sequence is considered red, since the illuminating elements which were active at that time, were illuminating elements $658_{RED}$. Similarly, the second detected frame 666 in an illumination sequence is considered green, since the illuminating elements, which were active at that time, were illuminating elements $658_{GREEN}$. Finally, the last detected frame 668 in an illumination sequence is considered blue, since the illuminating elements, which were active at that time, were illuminating elements $658_{BLUE}$. It is noted that any other combination of colors is applicable for this and any other aspect of the present invention, such as CYMG, and the like.

Figure 15:
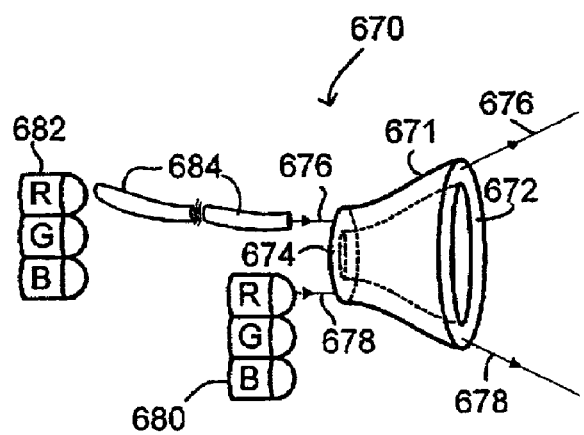
FIG. 15 is an illustration in perspective of a color illumination unit, constructed and operative in accordance with a further preferred embodiment of the present invention.

Reference is now made to FIG. 15, which is an illustration in perspective of a color illumination unit, generally referenced 670, constructed and operative in accordance with a further preferred embodiment of the present invention. Unit 670 includes a light-guiding element 671, which is generally shaped as an open-cut hollow cone, having a narrow section 674 and a wide section 672. A detection head according to the invention, such as described in FIG. 2 (referenced 202), can be placed within the hollow space of the light-guiding element 671. A multi-color light source 680 can be connected to the narrow section 674. Light, such as light ray 678, which is emitted from the light source 680, is directed via the light guiding element 671, and is projected through the wide section 672.

According to a further aspect of the invention, a remote multi-color light source 682 can be connected to the narrow section 674 via additional light guiding members such as optic-fibers 684. Light, such as light ray 676, which is emitted from the light source 682, is directed via the light guiding members 684 to the narrow section 674. The light-guiding element 671 guides light ray 676, and projects it through the wide section 672. This arrangement is useful when using an external light source, which is to be placed outside the inspected area (for example, outside the body of the patient).

According to a further aspect of the invention, a full spectrum illumination unit, which produces white light, is combined with a device such as sensor assembly 202 (FIG. 2).

Figure 16:
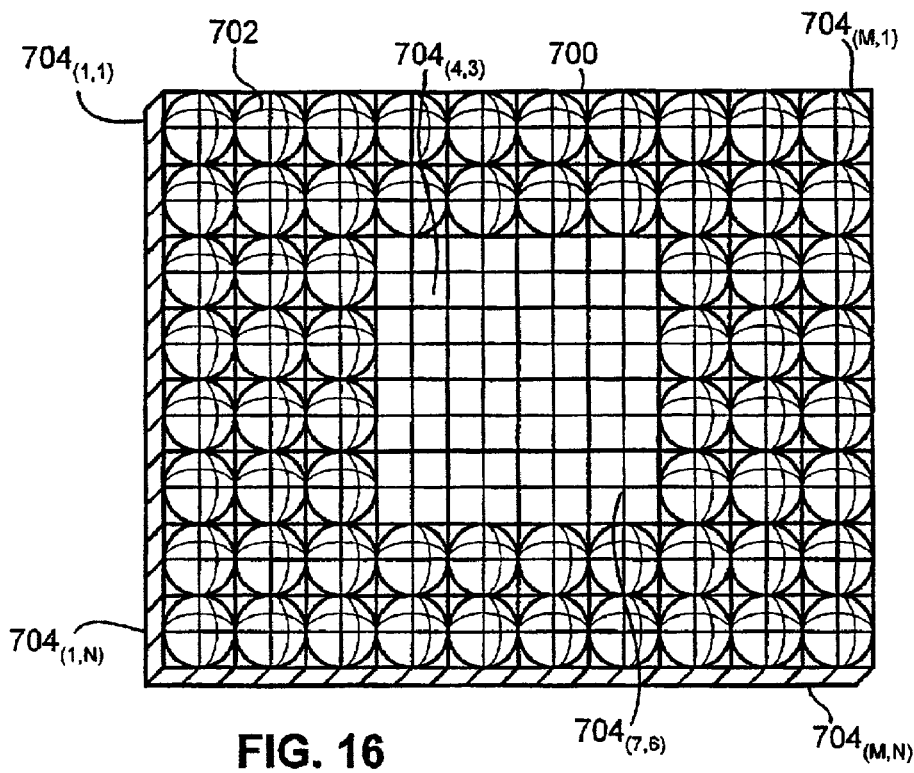
FIG. 16 is a view in perspective of a sensor array and a partial lenticular lens layer, constructed and operative in accordance with another preferred embodiment of the present invention.

Reference is now made to FIG. 16, which is a view in perspective of a sensor array, generally referenced 700, and a partial lenticular lens layer, generally referenced 702, constructed and operative in accordance with another preferred embodiment of the present invention. The partial lenticular lens layer 700 includes a plurality of four direction lenticular elements 702 such as described in FIGS. 9A and 10. The sensor array 700 is logically divided into a plurality of sensor sections, generally referenced $704_{(x,y)}$. For example, the upper left sensor section is referenced $704_{(1,1)}$ and the lower-right sensor section is referenced $704_{(M,N)}$. Some of the sensor sections, in the perimeter, are located beneath lenticular elements and others, such as the sensor sections in the center rectangle, which is defined by sensor sections $704_{(4,3)}$–$704_{(7,6)}$ are not. Accordingly, the sensors which are located at the center rectangle can not be used to provide multi-direction (stereoscopic or quadroscopic) information. Instead, these sensors provide enhanced resolution monoscopic information.

Figure 17:
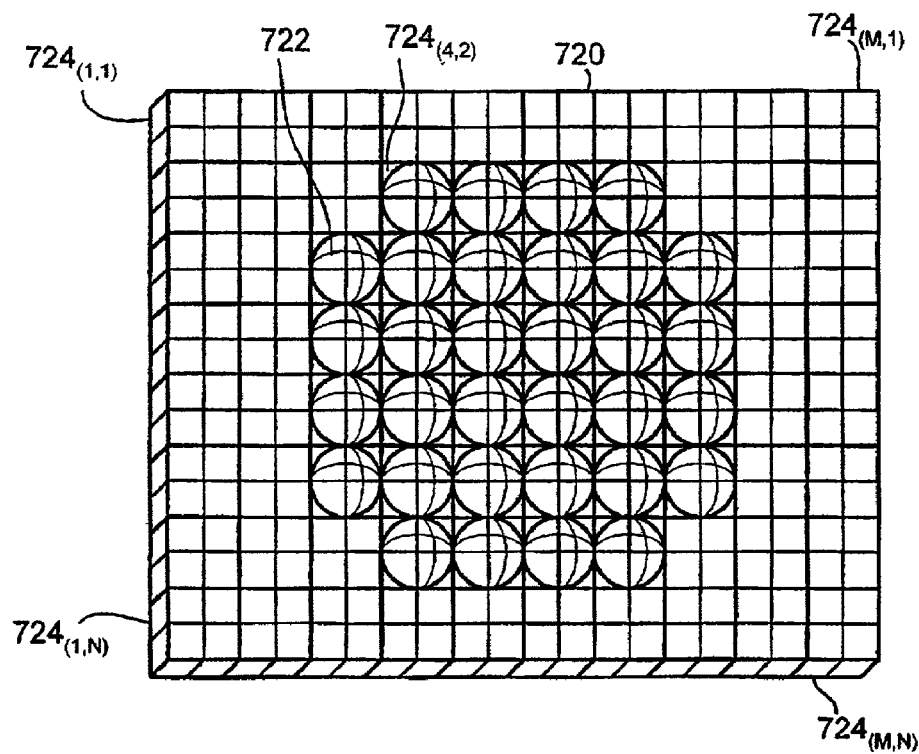
FIG. 17 is a view in perspective of a sensor array and a partial lenticular lens layer, constructed and operative in accordance with a further preferred embodiment of the present invention.

Reference is now made to FIG. 17, which is a view in perspective of a sensor array, generally referenced 720, and a partial lenticular lens layer, generally referenced 722, constructed and operative in accordance with a further preferred embodiment of the present invention. The partial lenticular lens layer 720 includes a plurality of four direction lenticular elements such as described in FIGS. 9A and 10. The sensor array 720 is logically divided into a plurality of sensor sections, generally referenced $724_{(x,y)}$. For example, the upper left sensor section is referenced $724_{(1,1)}$ and the lower-right sensor section is referenced $724_{(M,N)}$. Here, some of the sensor sections, in the center, (such as sensor section $724_{(4,2)}$) are located beneath lenticular elements and others, such as the sensor sections in the perimeter (such as sensor section $724_{(1,1)}$) are not. Accordingly, the sensors which are located at the center provide multi-direction (stereoscopic or quadroscopic) information and the ones in the perimeter provide enhanced resolution monoscopic information.

Figure 18:
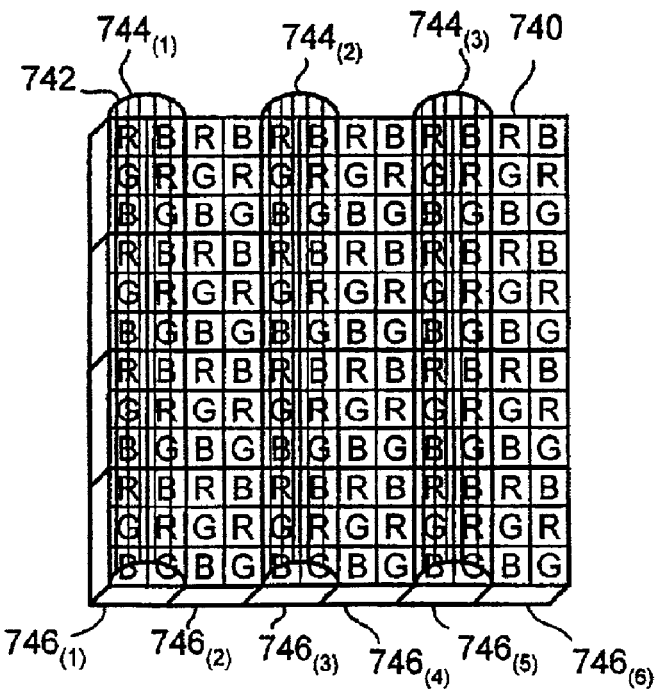
FIG. 18 is a schematic illustration of a sensor array and a partial lenticular lens layer, constructed and operative in accordance with another preferred embodiment of the present invention.

In accordance with a further aspect of the present invention there is provided a partial lenticular lens layer, which includes spaced apart lenticular elements. Reference is now made to FIG. 18, which is a schematic illustration of a sensor array, generally referenced 740, and a partial lenticular lens layer, generally referenced 742, constructed and operative in accordance with another preferred embodiment of the present invention.

The partial lenticular lens layer 742 includes a plurality of lenticular elements designated $744_{(1)}$, $744_{(2)}$ and $744_{(3)}$. Lenticular element $744_{(1)}$ is located over the first two left columns of color sensors, generally referenced $746_{(1)}$, of sensor array 740. Hence, the information received from these first two left columns of color sensors of sensor array 740 contains stereoscopic information. The third and fourth columns of color sensors, generally designated $746_{(2)}$, of sensor array 740 do not have a lenticular element located thereon, and hence, cannot be used to provide stereoscopic information.

Similarly, lenticular elements $744_{(2)}$ and $744_{(3)}$ are located over color sensor column pairs, $746_{(3)}$ and $746_{(5)}$, respectively, while color sensor column pairs, $746_{(4)}$ and $746_{(6)}$ are not covered with lenticular elements.

Figure 19:
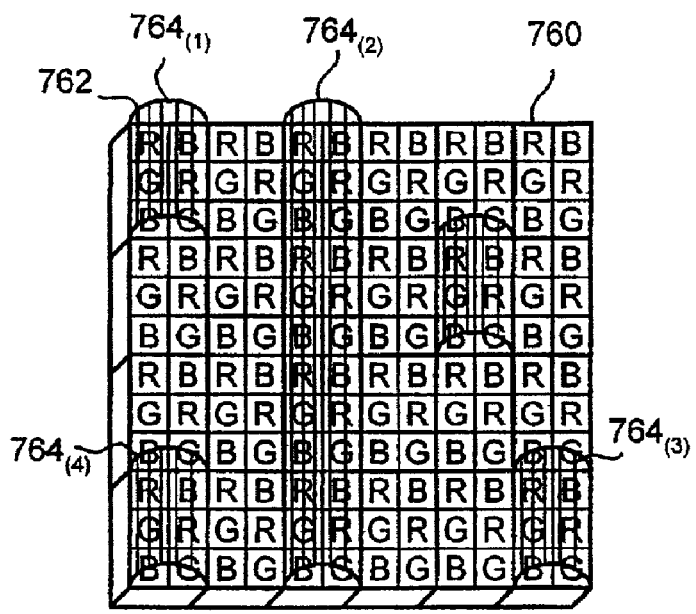
FIG. 19 is a schematic illustration of a sensor array and a partial lenticular lens layer, constructed and operative in accordance with a further preferred embodiment of the present invention.

Reference is now made to FIG. 19, which is a schematic illustration of a sensor array, generally referenced 760, and a partial lenticular lens layer, generally referenced 762, constructed and operative in accordance with another preferred embodiment of the present invention. Lenticular lens layer 762 includes a plurality of lenticular elements, referenced $764_{(1)}$, $764_{(2)}$, $764_{(3)}$ and $764_{(4)}$, being of different sizes and located at random locations over the sensor array 760. It is noted that any structure of partial lenticular lens layer is applicable for the invention, whereas the associated image processing application has to be configured according to the coverage of that specific lenticular lens layer, and to address covered sensors and uncovered sensors appropriately.

In accordance with a further aspect of the present invention, there is provided a system, which produces a color stereoscopic image. The structure of the stereoscopic device defines at least two viewing angles, through which the detector can detect an image of an object. According to one aspect of the invention, the stereoscopic device includes an aperture for each viewing angle. Each of the apertures can be opened or shut. The stereoscopic device captures a stereoscopic image, by alternately detecting an image of an object, from each of the viewing angles, (e.g., by opening a different aperture at a time and shutting the rest) through a plurality of apertures, (at least two), each time from a different aperture. The final stereoscopic image can be reconstructed from the images captured with respect to the different viewing angles.

The detection of stereoscopic color image is provided by illuminating the object with a sequence of light beams, each at a different wavelength, and detecting a separate image for each wavelength and aperture combination.

Figure 20A:
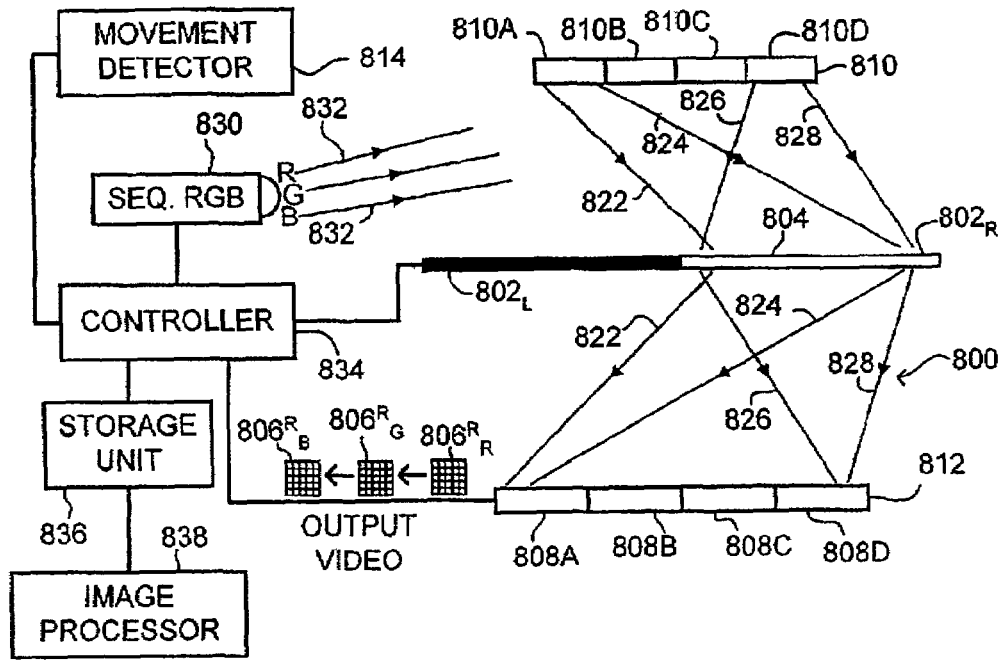
FIG. 20A is a schematic illustration of a system, for producing a color stereoscopic image, in a right side detection mode, constructed and operative in accordance with another preferred embodiment of the invention.
Figure 20B:
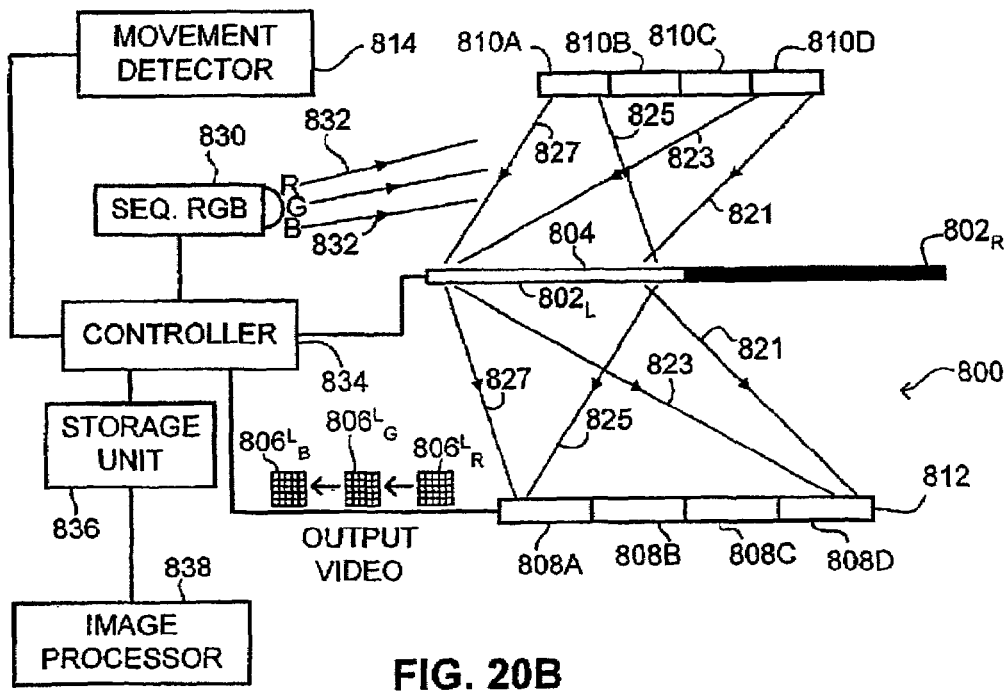
FIG. 20B is an illustration of the system of FIG. 20A, in a left-side detection mode.

Reference is now made to FIGS. 20A and 20B. FIG. 20A is a schematic illustration of a system, generally referenced 800, for producing a color stereoscopic image, in a right side detection mode, constructed and operative in accordance with a further preferred embodiment of the invention. FIG. 20B is an illustration of the system of FIG. 20A, in a left-side detection mode.

System 800 includes a multiple aperture 804, a controller 834, an image detector 812, a storage unit 836, an image processor 838, a movement detector 814 and an illumination unit 830. The controller 834 is connected to the multiple aperture 804, the image detector 812, the storage unit 836, movement detector 814 and to the illumination unit 830. The storage unit 836 is further connected to the image processor 838. The multiple aperture 804 includes a plurality of apertures, generally referenced $802_i$, where each aperture can be activated to be open or closed. It is noted that when an aperture is open it is at least transparent to a predetermined degree to light, and when an aperture is closed, it substantially prevents the travel of light there through. Any type of controllable light valve can be used to construct each of the apertures. Movement detector 814 detects the movement of image detector 812. The detected movement can be a linear displacement, an angular displacement, and the derivatives thereof such as velocity, acceleration, and the like. The operation of system 800, according to data received from movement detector 814, is described herein below in connection with FIGS. 25A, 25B, 25C, 26A, 26B and 26C.

Light valve elements are components, which have an ability to influence light in at least one way. Some of these ways are, for example: scattering, converging, diverging, absorbing, imposing a polarization pattern, influencing a polarization pattern which, for example, may be by rotation of a polarization plane. Other ways to influence light can be by influencing wave-length, diverting the direction of a beam, for example by using digital micro-mirror display (also known as DMD) or by using field effect, influencing phase, interference techniques, which either block or transfer a portion of a beam of light, and the like. Activation of light valve elements, which are utilized by the present invention, can be performed either electrically, magnetically or optically. Commonly used light valve elements are liquid crystal based elements, which either rotate or create and enforce a predetermined polarization axis.

In the present example, multiple aperture 804 includes two apertures $802_R$ and $802_L$. The controller 834 further activates the multiple aperture 804, so as to alternately open apertures $802_R$ and $802_L$. In FIG. 20A, aperture $802_R$ is open while aperture $802_L$ is closed and in FIG. 20B, aperture $802_R$ is closed while aperture $802_L$ is open.

Light rays, which reflect from various sections of the object 810, pass through the currently open aperture ($802_R$ in FIGS. 20A and $802_L$ in FIG. 20B). Thereby, light rays 822 and 824 arrive from section 810A of object 810, pass through aperture $802_R$, and are detected by detection element 808A, while light rays 826 and 828 arrive from section 810D, pass through aperture $802_R$ and are detected by detection element 808D. Hence, when aperture $802_R$ is open, the system 800 provides a right side view of the object 810.

With reference to FIG. 20B, when aperture $802_L$ is open, light rays 827 and 825 arrive from section 810A, pass through aperture $802_L$, and are detected by detection element 808A, while light rays 821 and 823 arrive from section 810D, pass through aperture 802L, and are detected by detection element 808D. Thereby, the system 800 provides a left side view of the object 810.

The illumination unit 830 is a multi-color illumination unit, which can produce light at a plurality of wavelengths. The controller 834 provides a sequence of illumination commands to the illumination unit 830, so as to produce a beam at a different predetermined wavelength, at each given moment. In the present example, the illumination unit is a red-green-blue (RGB) unit, which can produce a red light beam, a green light beam and a blue light beam. It is noted that illumination unit 830 can be replaced with any other multi-color illumination unit, which can produce either visible light, non-visible light or both, at any desired wavelength combination (CYMG and the like).

Furthermore, illumination unit 830 can be a passive unit, where it receives external commands to move from one wavelength to another, or it can be an active unit, which changes wavelength independently and provides an indication of the currently active wavelength to an external controller. Illumination unit 830 of the present example is a passive unit, which enhances the versatility of the system 800, by providing any wavelength sequence on demand.

The image detector 812 includes a plurality of detection elements 808A, 808B, 808C and 808D. In accordance with one aspect of the invention, image detector 812 is a full range color detector, where each of the detection elements is operative to detect light in a plurality of wavelengths. In accordance with another aspect of the invention, the image detector 812 is a color segmented detector, where the detection elements are divided into groups, each operative to detect light in a different range of wavelengths. One conventional type of such detectors includes a full range detection array, which is covered by a color filter layer, where each detection element is covered by a different color filter. Accordingly, some of the detection elements are covered with red filters, others are covered with green filters and the rest are covered with blue filters.

The present invention enhances the color resolution of systems, using such color detectors. It will be appreciated by those skilled in the art that a color segment detector of poor quality may exhibit a wavelength (color) overlap between the different detection elements. For example, when the filters are of poor quality, their filtering functions tend to overlap such that the red filter also passes a small amount of either green or blue light. Hence, the detection element behind the red filter, also detects that small amount of green or blue light, but provides an output measurement as a measurement of red light. Hence, the color detector produces an image, which includes incorrect measurements of red light (e.g. more than the actual red light, which arrived at the detector) as result of that overlap. Accordingly, received information of the inspected object is not valid.

In the present invention, the illumination unit 830 produces a sequence of non-overlapping illumination beams at predetermined wavelengths (i.e., red, blue and green). As explained above, the color detector detects an image, which includes incorrect measurements, as a result of the wavelength (color) filtering overlap. Since the illumination unit 830 and the image acquisition process are synchronized, the imaging system can process each of the acquired images, according to the actual light beam color, which was produced therewith. For example, the illumination unit 830 produces blue light illumination beam. At the same time the image detector 812 detects an image, which also includes actual light measurements in detection elements, which are covered with green and red filters, due to the wavelength overlap. The imaging system can discard light measurements, which are received from detection elements, covered with color filters, which are not blue (e.g., red and green).

Such sequenced color illumination of the object, provides enhanced color resolution, for color image detectors of poor quality, and obtains the valid color images of the inspected object. System 800 can further include a stereoscopic display unit (not shown), connected to controller 834 for displaying an stereoscopic image of object 810.

Figure 21A:
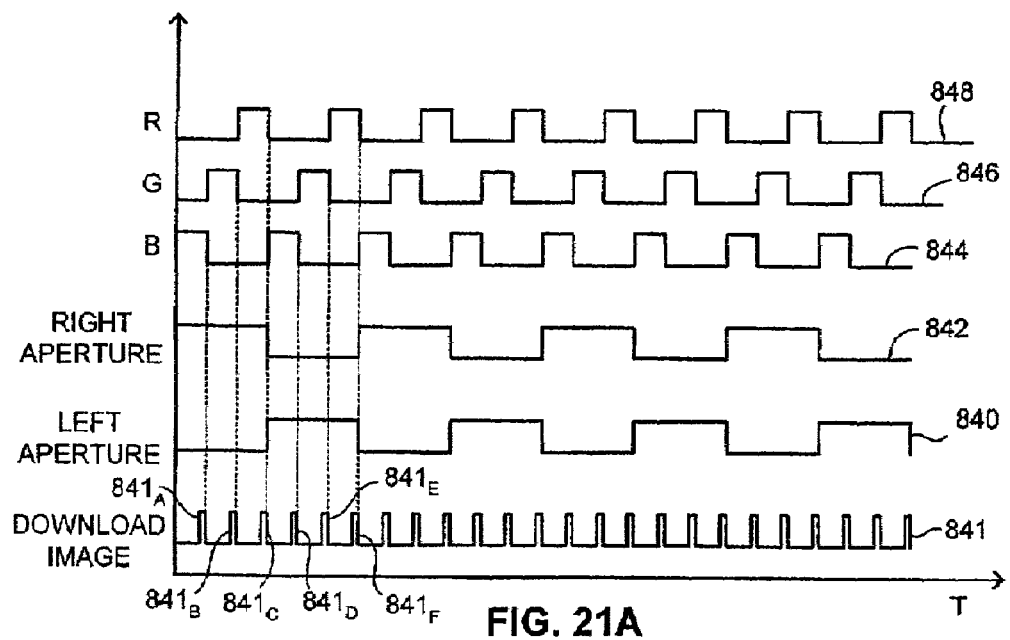
FIG. 21A is a schematic illustration of a timing sequence, in which the controller of the system of FIG. 20A synchronizes the operation of illumination unit, apertures and image detector of that same system.

Reference is further made to FIG. 21A, which is a schematic illustration of a timing sequence, in which controller 834 (FIG. 20A) synchronizes the operation of illumination unit 830, apertures $802_L$ and $802_R$, and image detector 812. Signal 840 represents the timing sequence of the left aperture $802_L$. Signal 842 represents the timing sequence of the right aperture $802_R$. Signal 844 represents the timing sequence of the blue light beam, produced by the illumination unit 830. Signal 846 represents the timing sequence of the green light beam, produced by the illumination unit 830. Signal 848 represents the timing sequence of the red light beam, produced by the illumination unit 830. Signal 841 represents the timing sequence of the image detector 812, where each image is downloaded therefrom.

Timing sequence 841 rises every time any of the rises of sequences 844, 846 and 848 intersect with a rise of either sequence 842 or sequence 840. For example, rise $841_A$ indicates a frame download of a blue light-right aperture combination, rise $841_B$ indicates a frame download of a green light-right-aperture combination, and rise $841_C$ indicates a frame download of a red light-right aperture combination. Similarly, rise $841_D$ indicates a frame download of a blue light-left aperture combination, rise $841_E$ indicates a frame download of a green light-left aperture combination and rise $841_F$ indicates a frame download of a red light-left aperture combination.

It is noted that for some light sources, the produced light beams do not cover the full range of visible light. For such light sources, the missing color components can be reconstructed (interpolated) taking into consideration the physiological assumption, that color reflection response as a function of reflected angle, does not change much with angle.

Figure 22:
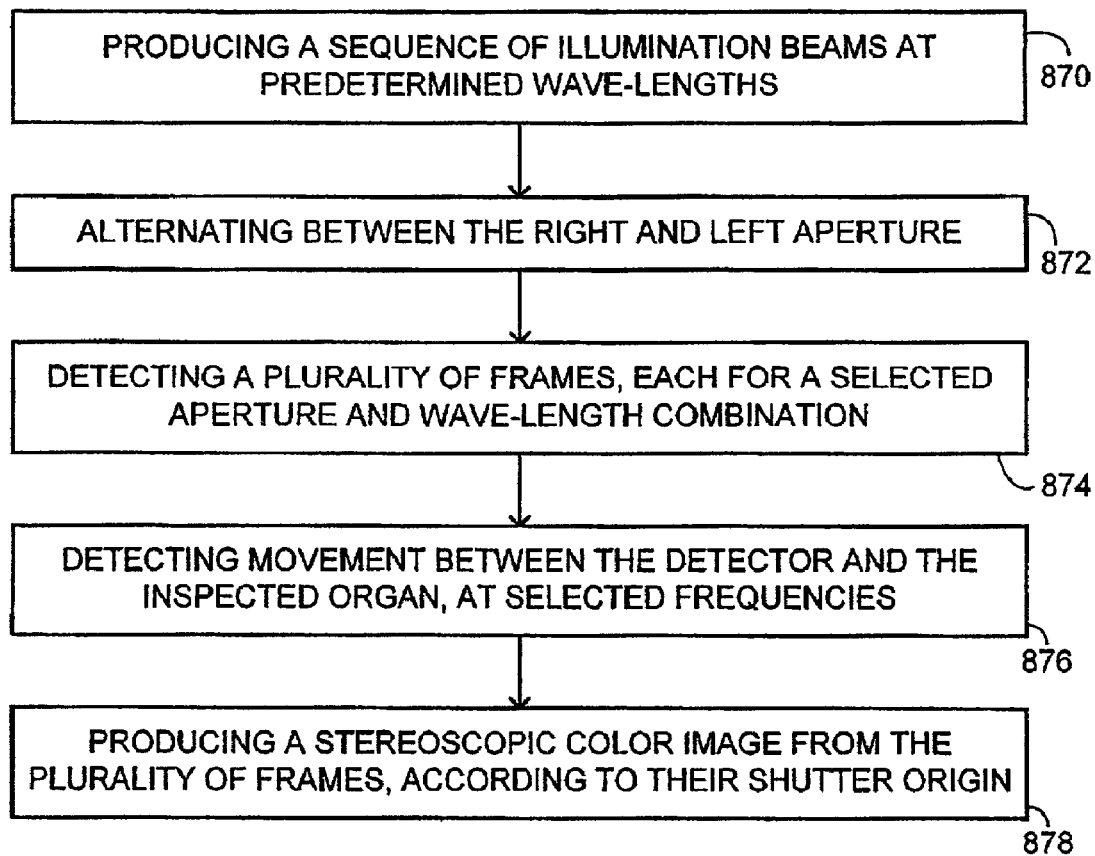
FIG. 22 is a schematic illustration of a method for operating the system of FIGS. 20A and 20B, operative in accordance with a further preferred embodiment of the present invention.

Reference is further made to FIG. 22, which is a schematic illustration of a method for operating system 800 of FIGS. 20A and 20B, operative in accordance with another preferred embodiment of the present invention. In step 870, a sequence of illumination beams at predetermined wavelengths is produced. With reference to FIGS. 20A and 20B, controller 834 provides a sequence of illumination commands to the illumination unit 830, which in turn produces different wavelength light beams, generally referenced 832, at predetermined points in time, towards an object, generally referenced 810.

In step 872 right and left apertures are alternated. Light rays, which reflect from various sections of the object 810, pass through the currently open aperture ($802_R$ in FIG. 20A and $802_L$ in FIG. 20B). With reference to FIGS. 20A and 20B, controller 834 provides a sequence of operating commands to the apertures $802_L$ and $802_R$.

In step 874, a plurality of frames, each for a selected aperture and wavelength combination is detected. Controller 834 operates the image detector 812 so as to detect a plurality of frames, each respective of a selected aperture and wavelength combination.

Light rays 822 and 824 (FIG. 20A) arrive from section 810A of object 810, pass through aperture $802_R$, and are detected by detection element 808A, while light rays 826 and 828 arrive from section 810D, pass through aperture $802_R$ and are detected by detection element 808D. It is noted that in the present example, an imaging element (not shown) is introduced in the vicinity of multiple aperture 804. Hence, when aperture $802_R$ is open, the system 800 provides a right side view of the object 810.

Light rays 827 and 825 (FIG. 20B) arrive from section 810A, pass through aperture $802_L$ and are detected by detection element 808A, while light rays 821 and 823 arrive from section 810D, pass through aperture $802_L$ and are detected by detection element 808D. Hence, when aperture $802_L$ is open, the system 800 provides a left side view of the object 810.

With reference to FIG. 21A, rise $841_A$ provides a right side blue image (reference $806^R_G$ of FIG. 20A), rise $841_B$ provides a right side green image (reference $806^R_G$ of FIG. 20A), and rise $841_C$ provides a right side red image (reference $806^R_R$ of FIG. 20A). Similarly, rise $841_D$ provides a left side blue image (reference $806^L_B$ of FIG. 20B), rise $841_E$ provides a left side green image (reference $806^L_G$ of FIG. 20B), and rise $841_F$ provides a left side red image (reference $806^L_R$ of FIG. 20B). With reference to FIGS. 20A and 20B, image detector 812 detects the plurality of frames, and provides right and left output video for image processing.

In step 876, movement between the detector and the inspected organ, at selected frequencies is detected. This movement can be detected from movement of the endoscope, by means of a movement detector, or by analyzing the detected images, where different color images exhibit different lines, with dramatic color shade changes. This information is utilized in the following step, for spatially correlating between images of different colors.

In step 878 a stereoscopic color image from the plurality of frames, according to their aperture origin is produced. With reference to FIGS. 20A and 20B, the controller 834 stores the detected images in storage unit 836. Image processor 838 retrieves the detected images from the storage unit 836, and constructs color stereoscopic images. Hence, the present invention provides an additional way for detecting a color stereoscopic image, using a single image detector for both sides and all colors.

Figure 21B:
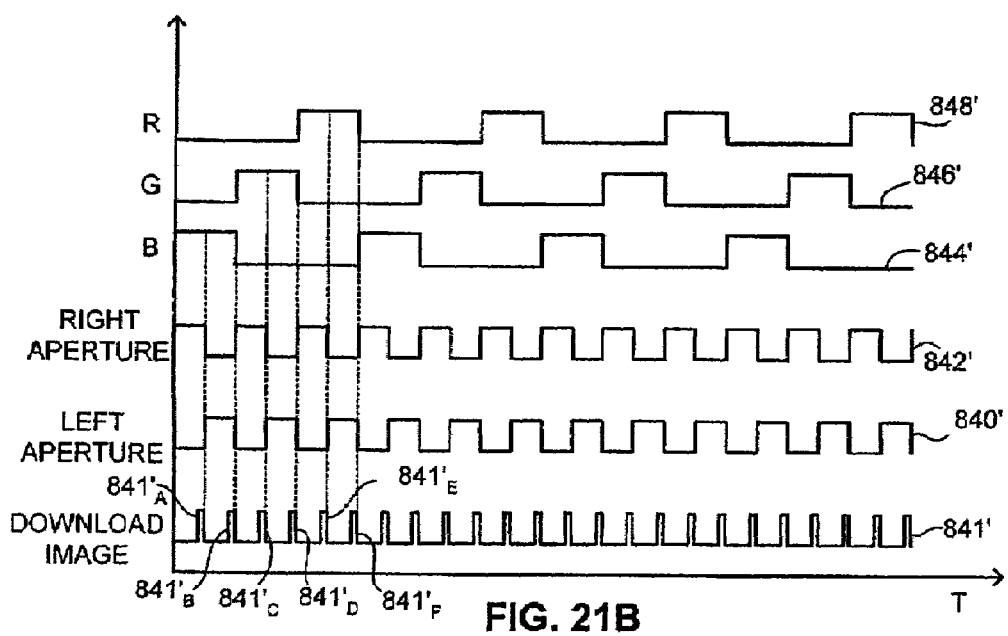
FIG. 21B is a schematic illustration of another timing sequence, in which the controller of FIG. 20A synchronizes the operation of the illumination unit, right and left apertures and the image detector.

Reference is further made to FIG. 21B, which is a schematic illustration of another timing sequence, in which controller 834 (FIG. 20A) synchronizes the operation of illumination unit 830, apertures $802_L$ and $802_R$, and image detector 812. Signal 840' represents the timing sequence of the left aperture $802_L$. Signal 842' represents the timing sequence of the right aperture $802_R$. Signal 844' represents the timing sequence of the blue light beam, produced by the illumination unit 830. Signal 846' represents the timing sequence of the green light beam, produced by the illumination unit 830. Signal 848' represents the timing sequence of the red light beam, produced by the illumination unit 830. Signal 841' represents the timing sequence of the image detector 812, where each image is downloaded therefrom.

Timing sequence 841' rises every time any of the rises of sequences 844', 846' and 848' intersects with a rise of either sequence 842' or sequence 840'. For example, rise $841'_A$ indicates a frame download of a blue light right aperture combination, rise $841'_B$ indicates a frame download of a blue light-left aperture combination and rise $841'_C$ indicates a frame download of a green light-right aperture combination. Similarly, rise $841'_D$ indicates a frame download of a green light-left aperture combination, rise $841'_E$ indicates a frame download of a red light-right aperture combination and rise $841'_F$ indicates a frame download of a blue light-left aperture combination.

Figure 23:
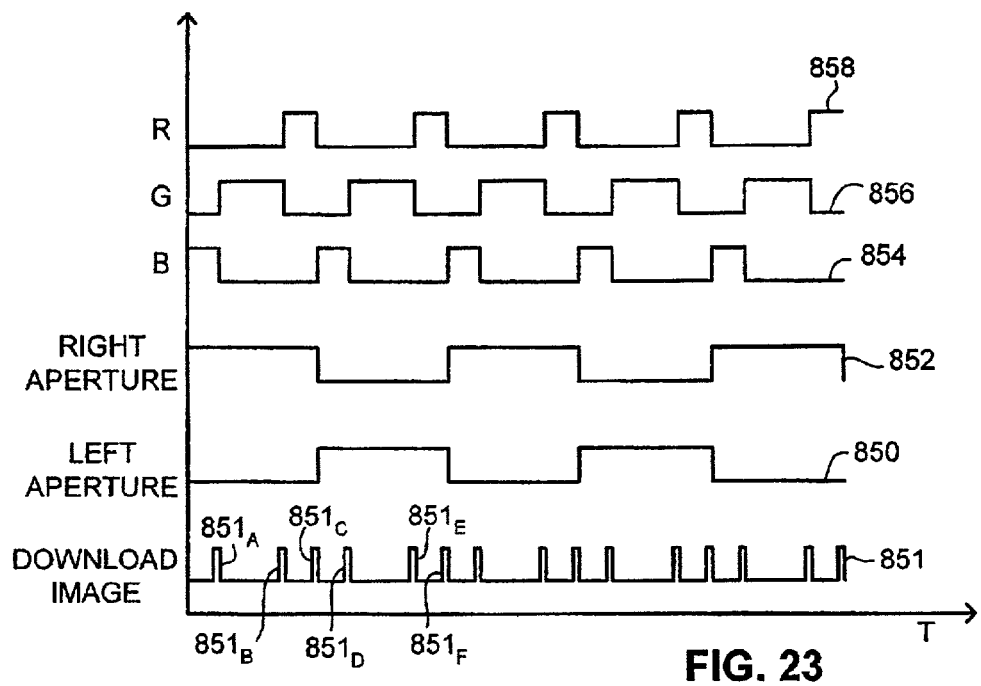
FIG. 23 is a schematic illustration of a timing scheme, for operating the system of FIGS. 20A and 20B, in accordance with another preferred embodiment of the present invention.

Reference is further made to FIG. 23, which is a schematic illustration of a timing scheme, for operating system 800 of FIGS. 20A and 20B, in accordance with a further preferred embodiment of the present invention. Signal 850 represents the timing sequence of the left aperture $802_L$. Signal 852 represents the timing sequence of the right aperture $802_R$. Signal 854 represents the timing sequence of the blue light beam. Signal 856 represents the timing sequence of the green light beam. Signal 858 represents the timing sequence of the red light beam. Signal 851 represents the timing sequence of the image detector 812, where each image is downloaded therefrom. As can be seen in FIG. 23, the timing scheme is asymmetric, where the green light beam is activated for a time period which is twice the time period of either the red light beam or the blue light beam. Signal 851 corresponds to this arrangement and provides a green image download rise (references $851_B$ and $851_E$), after a time period which is twice as long with comparison to red image download rises (references $851_C$ and $851_F$) or blue image download rises (references $851_A$ and $851_D$).

Figure 24:
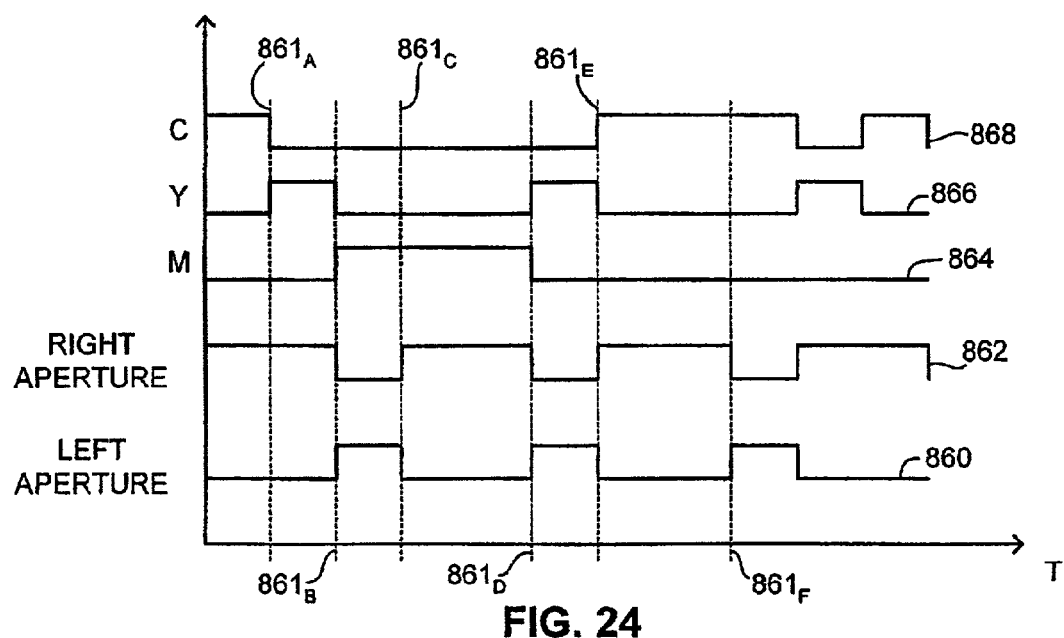
FIG. 24 is a schematic illustration of a timing scheme, for operating the system of FIGS. 20A and 20B, in accordance with a further preferred embodiment of the present invention.

Reference is further made to FIG. 24, which is a schematic illustration of a timing scheme, for operating system 800 of FIGS. 20A and 20B, in accordance with another preferred embodiment of the present invention. Signal 860 represents the timing sequence of the left aperture $802_L$. Signal 862 represents the timing sequence of the right aperture $802_R$. Signal 864 represents the timing sequence of the magenta light beam. Signal 866 represents the timing sequence of the yellow light beam. Signal 868 represents the timing sequence of the cyan light beam. As can be seen in FIG. 24, the timing scheme addresses an alternate wavelength scheme and is also asymmetric.

It is noted that a mechanical multi-wavelength illumination unit such as described in the prior art, can be used for implementing the present invention. However, such a system significantly reduces the capability of the user to control illumination duration, wavelength ratio and detection timing, such as described herein above.

The disclosed technique incorporates even more advanced aspects, which provide automatic image translation correction, based on correlation between the two detected images. When the endoscope is handheld, it is subjected to the vibration of the human hand, which is in the order of 10 Hz, at an angular amplitude of 1 degree. This phenomenon causes a blur of areas, where different colors intersect, and is also known as the "between color field blur" effect. It is noted that any movement between the image detector and the inspected organ can cause this phenomenon, provided it occurs at particular frequencies, defined by the structure and the manner of operation of the system.

With reference to FIGS. 20A and 20B, since the information retrieved from image detector 812 relates to specific colors, then controller 834 can correlate between such single color images to determine the ΔX and ΔY to the subsequent color, and hence compose and produce an un-blurred color image. Due to the vibrations of the human hand, while image detector 812 is substantially stationary relative to object 810, the displayed stereoscopic image of object 810 is blurred. In order to mitigate this problem, and provide a blur-free stereoscopic image of object 810 to the viewer, movement detector 230 (FIG. 2), is incorporated with system 200, and movement detector 814 is incorporated with system 800.

Figure 25C:
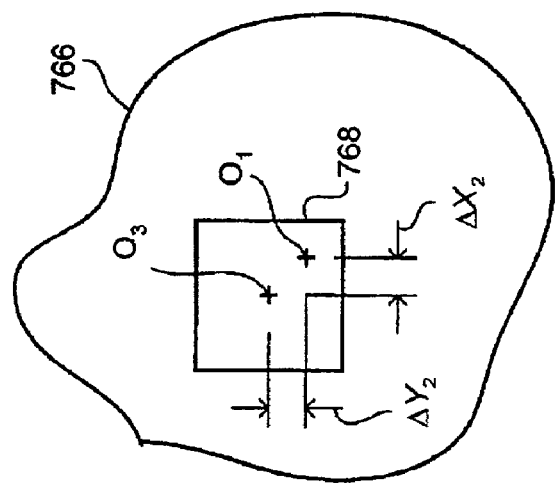
FIG. 25C is a schematic illustration of the object and the sensor assembly of FIG. 25A, when the sensor assembly has moved to another position.
Figure 25B:
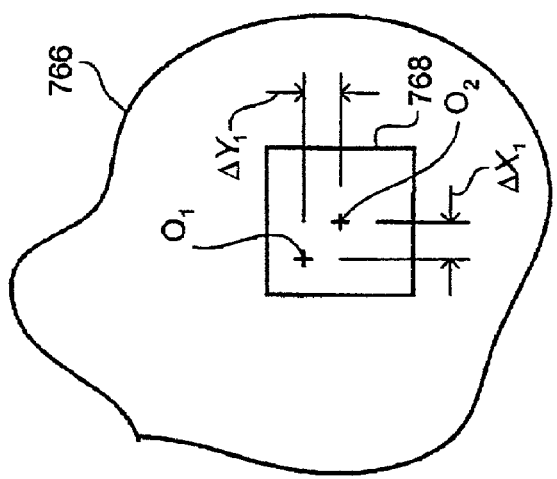
FIG. 25B is a schematic illustration of the object and the sensor assembly of FIG. 25A, when the sensor assembly has moved to a new position.
Figure 25A:
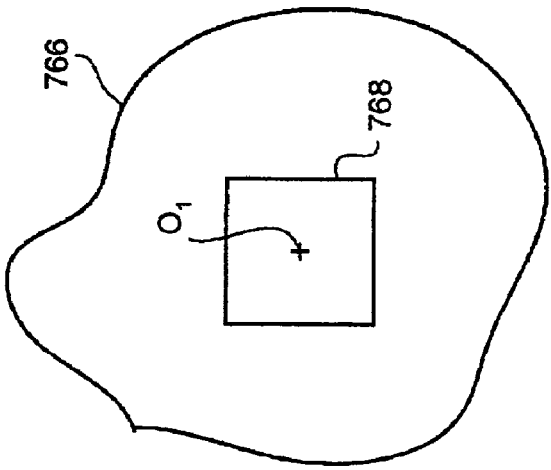
FIG. 25A is a schematic illustration of an object and a sensor assembly, when the sensor assembly is located at an initial position with respect to the object.
Figure 26A:
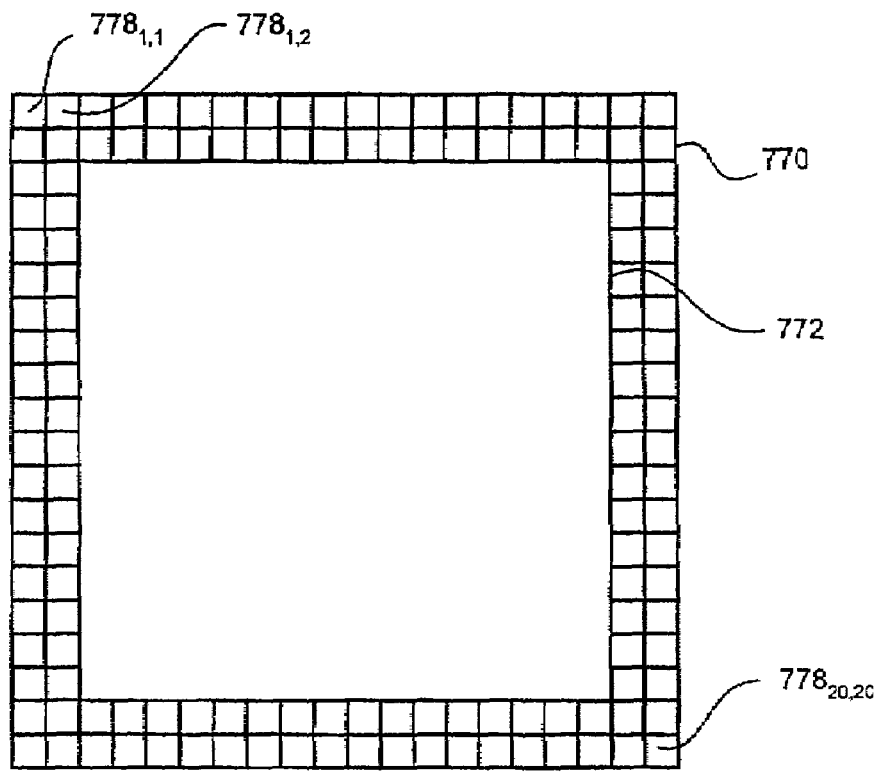
FIG. 26A is a schematic illustration of a detected image, as detected by sensor assembly of FIG. 25A, and a respective displayed image, in accordance with a further preferred embodiment of the present invention.
Figure 26B:
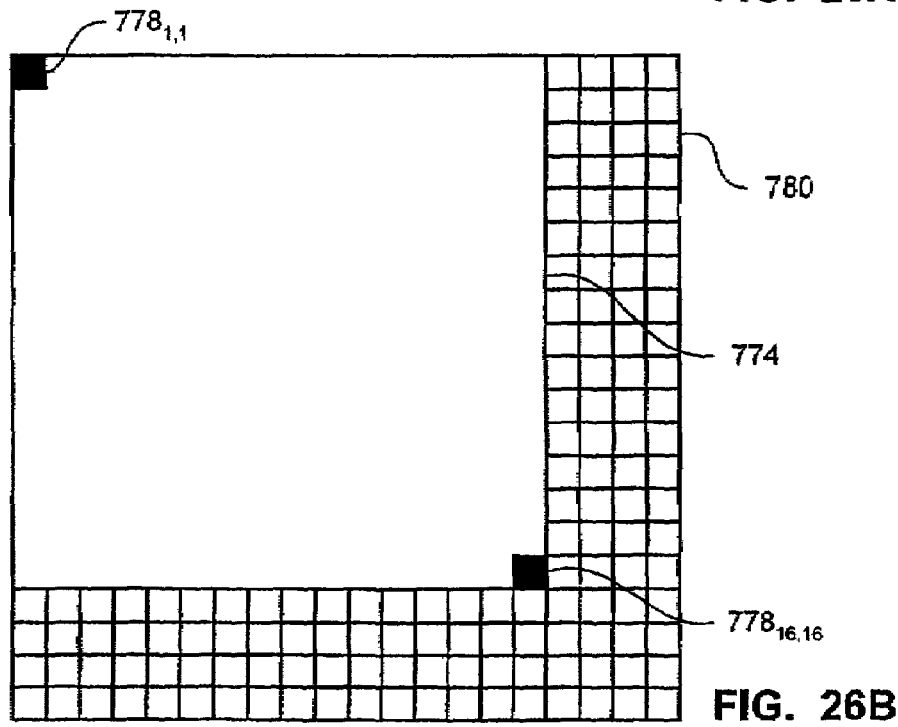
FIG. 26B is a schematic illustration of a detected image, as detected by sensor assembly of FIG. 25B, and a respective displayed image.
Figure 26C:
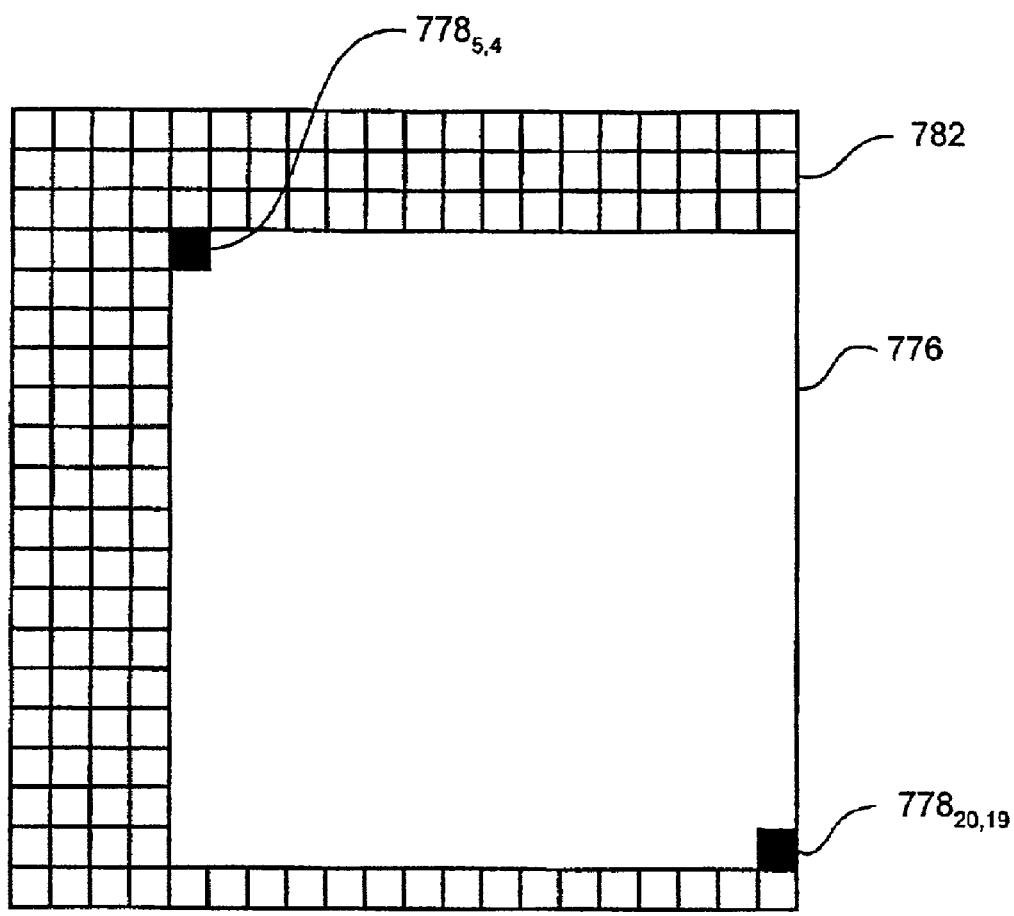
FIG. 26C is a schematic illustration of a detected image, as detected by the sensor assembly of FIG. 25C, and a respective displayed image.

Reference is now made to FIGS. 25A, 25B, 25C, 26A, 26B and 26C and again to FIG. 2. FIG. 25A is a schematic illustration of an object, generally referenced 766, and a sensor assembly generally referenced 768, when the sensor assembly is located at an initial position with respect to the object. FIG. 25B is a schematic illustration of the object and the sensor assembly of FIG. 25A, when the sensor assembly has moved to a new position. FIG. 25C is a schematic illustration of the object and the sensor assembly of FIG. 25A, when the sensor assembly has moved to another position. FIG. 26A is a schematic illustration of a detected image, generally referenced 770, as detected by sensor assembly of FIG. 25A, and a respective displayed image, generally referenced 772, in accordance with a further preferred embodiment of the present invention. FIG. 26B is a schematic illustration of a detected image, generally referenced 780, as detected by sensor assembly of FIG. 25B, and a respective displayed image, generally referenced 774. FIG. 26C is a schematic illustration of a detected image, generally referenced 782, as detected by the sensor assembly of FIG. 25C, and a respective displayed image, generally referenced 776.

The foregoing description relates to one aspect of the invention, in which an stereoscopic image of an object is captured by a sensor array through a lenticular lens layer (i.e., each captured image includes all the primary colors of the color palette, such as RGB, CYMG, and the like). It is noted that the movement is determined such that it has a constant average (e.g., vibrating about a certain point).

With reference to FIGS. 25A and 26A, the center of sensor assembly 768 is located at a point $O_1$ relative to object 766. Sensor assembly 768 detects detected image 770 (FIG. 26A) of object 766, where the detected image 770 is composed for example, of four hundred pixels (i.e., a 20×20 matrix). Each pixel is designated by $P_{m,n}$ where m is the row and n is the column of detected image 770. For example, pixel $778_{1,1}$ is located in the first row and the first column of detected image 770, pixel $778_{1,2}$ is located in the first row and the second column, and pixel $778_{20,20}$ is located in row twenty and column twenty. Processor 208 selects pixels $778_{3,3}$ through $778_{18,18}$ (i.e., a total of 16×16=256 pixels) to display the sub-matrix 772 on stereoscopic display 214 (FIG. 2), while the center of sensor assembly 768 is located at point $O_1$.

With reference to FIGS. 25B and 26B, due to the vibrations of the human hand, the center of sensor assembly 768 has moved to a point $O_2$ relative to object 766. Point $O_2$ is located a distance $\Delta X_1$ to the right of point $O_1$ and a distance $\Delta Y_1$ below point $O_1$. In this case the length of $\Delta X_1$ is equal to the horizontal width of two pixels of detected image 780, and the length $\Delta Y_1$ is equal to the vertical height of minus two pixels of detected image 780. Movement detector 230 detects the movement of sensor assembly 768 from point $O_1$ to point $O_2$, and sends a signal respective of this movement, to processor 208.

With reference to FIG. 26B, the image of the object section that was captured by sub-matrix 772, is now captured by a sub-matrix 774, which is shifted two pixels up and two pixels to the left. Hence, displaying sub-matrix 774, compensates for the movement of sensor assembly 768. For this purpose, processor 208 selects pixels $778_{1,1}$ through $778_{16,16}$ of detected image 780, for sub-matrix 774. Despite the movement of sensor assembly 768, the images of sub-matrices 772 and 774 are substantially of the same area, and therefore the user does not realize that sensor assembly 768 has moved from point $O_1$ to point $O_2$.

With reference to FIGS. 25C and 26C, the center of sensor assembly 768 has moved from point $O_1$ to a point $O_3$ relative to object 766. Point $O_3$ is located a distance $\Delta X_2$ to the left of point $O_1$ and a distance $\Delta Y_2$ above point $O_1$. In this case the length of $\Delta X_2$ is equal to the horizontal width of minus two pixels of detected image 782, and the length $\Delta Y_2$ is equal to the vertical height of one pixel of detected image 782. Movement detector 230 detects the movement of sensor assembly 768 from point $O_1$ to point $O_3$, and sends a signal respective of this movement, to processor 208.

With reference to FIG. 26C, the image of the object section that was captured by sub-matrix 772, is now captured by a sub-matrix 776, which is shifted one pixel up and two pixels to the left. Hence, displaying sub-matrix 774, compensates for the movement of sensor assembly 768 two pixels to the left and one pixel up. For this purpose, processor 208 selects pixels $778_{5,4}$ through $778_{20,19}$ of detected image 782, for sub-matrix 776. Despite the movement of sensor assembly 768, the images of displayed images 772 and 776 are identical, and therefore the user does not realize that sensor assembly 768 has moved from point $O_1$ to point $O_3$. Therefore, by incorporating movement detector 230 with sensor assembly 768, the viewer views a blur-free stereoscopic color image of object 766, despite the vibrations of sensor assembly 768 caused by the human hand.

It is noted that processor 208 processes the detected images 780 and 782, if the dimensions $\Delta X_1$, $\Delta X_2$, $\Delta Y_1$ and $\Delta Y_2$ are of the order of A, the amplitude of vibrations of the human hand and in the appropriate frequency. In general, processor 208 performs the compensation process, between a plurality of captured images, as long as the detected movement, is maintained about a certain average point ($X_{AVERAGE}$, $Y_{AVERAGE}$). When one of the average values $X_{AVERAGE}$ and $Y_{AVERAGE}$ changes, then processor 208 initiates a new compensation process around the updated average point, accordingly.

Figure 25F:
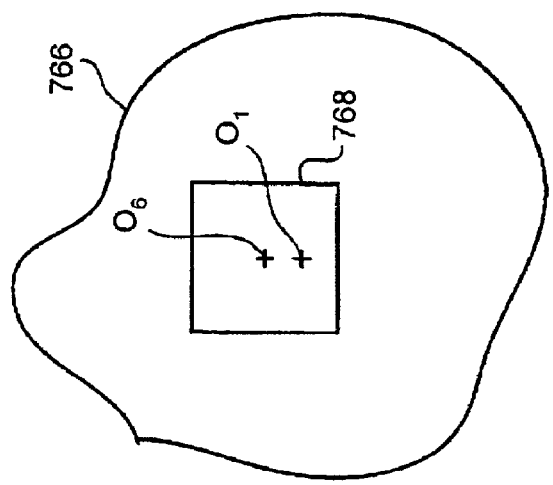
FIG. 25F is a schematic illustration of the object and the sensor assembly of FIG. 25A, when the sensor assembly has moved to a further new position.
Figure 25E:
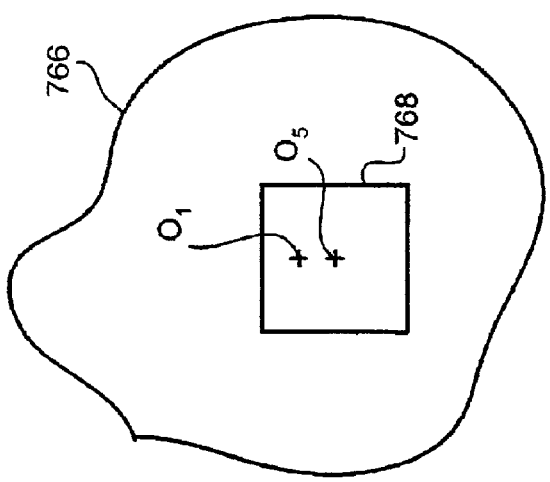
FIG. 25E is a schematic illustration of the object and the sensor assembly of FIG. 25A, when the sensor assembly has moved to another new position.
Figure 25D:
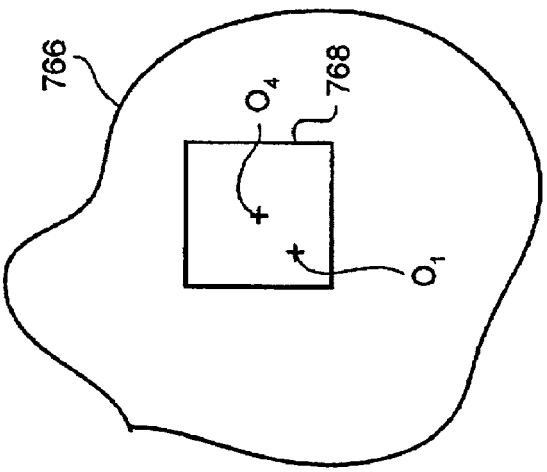
FIG. 25D is a schematic illustration of the object and the sensor assembly of FIG. 25A, when the sensor assembly has moved to a further new position.
Figure 27F:
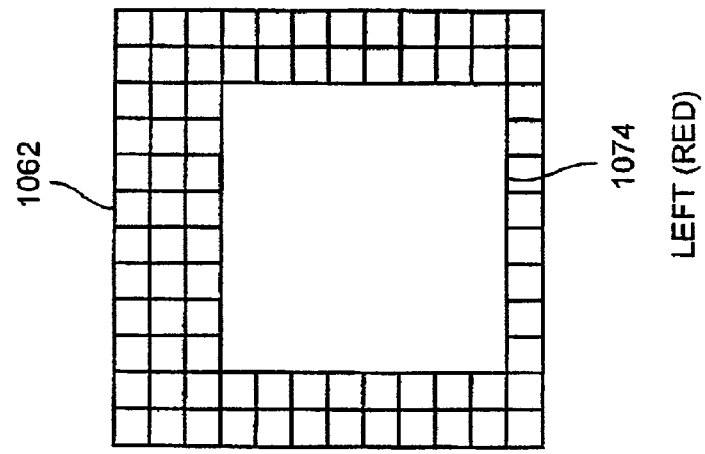
FIG. 27F is a schematic illustration of a sub-matrix, when the sensor assembly is at a location illustrated in FIG. 25F.
Figure 27E:
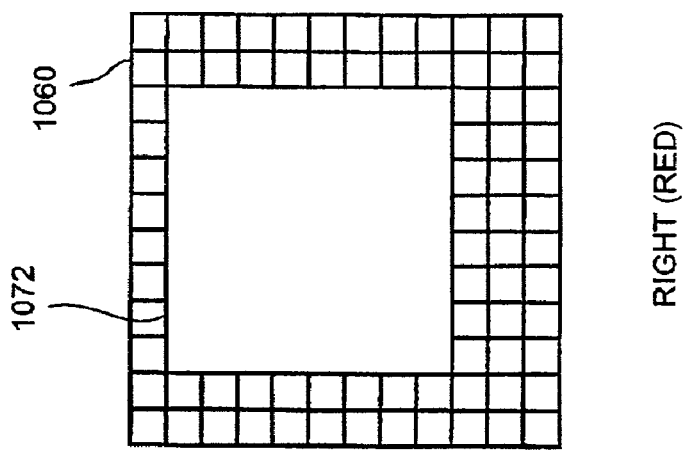
FIG. 27E is a schematic illustration of a sub-matrix, when the sensor assembly is at a location illustrated in FIG. 25E.
Figure 27D:
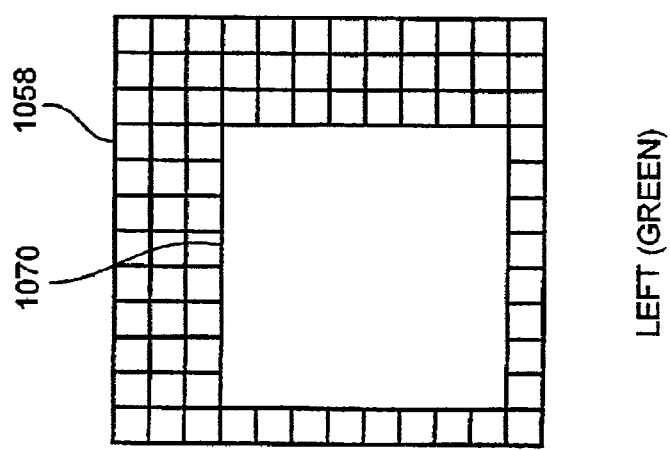
FIG. 27D is a schematic illustration of a sub-matrix, when the sensor assembly is at a location illustrated in FIG. 25D.

Reference is now made to FIG. 25D, 25E, 25F, 27A, 27B, 27C, 27D, 27E, 27F and again to FIGS. 20A, 20B, 25A, 25B and 25C. FIG. 25D is a schematic illustration of the object and the sensor assembly of FIG. 25A, when the sensor assembly has moved to a further new position. FIG. 25E is a schematic illustration of the object and the sensor assembly of FIG. 25A, when the sensor assembly has moved to another new position. FIG. 25F is a schematic illustration of the object and the sensor assembly of FIG. 25A, when the sensor assembly has moved to a further new position. FIG. 27A is a schematic illustration of a sub-matrix, generally referenced 1064, in accordance with another preferred embodiment of the present invention, when the sensor assembly is at a location illustrated in FIG. 25A. FIG. 27B is a schematic illustration of a sub-matrix, generally referenced 1066, when the sensor assembly is at a location illustrated in FIG. 25B. FIG. 27C is a schematic illustration of a sub-matrix, generally referenced 1068, when the sensor assembly is at a location illustrated in FIG. 25C. FIG. 27D is a schematic illustration of a sub-matrix, generally referenced 1070, when the sensor assembly is at a location illustrated in FIG. 25D. FIG. 27E is a schematic illustration of a sub-matrix, generally referenced 1072, when the sensor assembly is at a location illustrated in FIG. 25E. FIG. 27F is a schematic illustration of a sub-matrix, generally referenced 1074, when the sensor assembly is at a location illustrated in FIG. 25F.

Image processor 838 (FIG. 20A), selects each of sub-matrices 1064, 1066 and 1068 from detected images 1052, 1054 and 1056, respectively, as described herein above in connection with FIGS. 26A, 26B and 26C. Analogously, image processor 838 selects each of sub-matrices 1070, 1072 and 1074 from detected images 1058, 1060 and 1062, respectively, when the center of sensor assembly 768 is directed to each of the points $O_4$, $O_5$, and $O_6$, respectively. For example, when the center of sensor assembly 768 is directed to point $O_4$, which is located to the right and above point $O_1$, image processor 838 selects sub-matrix 1070 (FIG. 27D). When the center of sensor assembly 838 is directed to point $O_5$ directly below point $O_1$, image processor 838 selects sub-matrix 1072 (FIG. 27E). When the center of sensor assembly 838 is directed to point $O_6$ directly above point $O_1$, image processor 838 selects sub-matrix 1074 (FIG. 27F).

In the following description, object 810 (FIGS. 20A and 20B) and object 766 (FIG. 25A) are used interchangeably, although they both represent the same object. Object 810 is described in connection with multiple aperture 804 and illumination unit 830, while object 766 is described in connection with the location of sensor assembly 768 relative thereto. It is noted that during the time interval in which the opening of multiple aperture 804 switches from aperture $802_R$ (FIG. 20A), to aperture $802_L$ (FIG. 20B), sensor assembly 768 moves relative to object 766, due to the vibrations of the human hand. Thus, for example, sub-matrix 1064 (FIG. 27A) represents a right view image of object 810 corresponding to the image which image processor 838 captures, when aperture $802_R$ is open. On the other hand, sub-matrix 1066 (FIG. 27B) represents a left view image of object 766, when aperture $802_L$ is open.

Furthermore, the color of detected images 1052, 1054, 1056, 1058, 1060, and 1062 changes as described herein above for example in connection with FIG. 21B. Image processor 838 receives download image $841'_A$, and selects sub-matrix 1064 (FIG. 27A), which is a right view image of object 766 (FIG. 25A) in blue, when the center of sensor assembly 768 is directed to point $O_1$.

While multiple aperture 804 switches to aperture $802_L$, the center of sensor assembly 768 (FIG. 25B) directs to point $O_2$ (FIG. 25B), and image processor 838 receives download image $841'_B$. Since the center of sensor assembly 768 is directed to point $O_2$ (FIG. 25B), then image processor 838 selects sub-matrix 1066 (FIG. 27B) which represents a left view image of object 810 in blue. Analogously, sub-matrix 1068 (FIG. 27C) represents a green right view image of object 766 (download image $841'_C$), when the center of sensor assembly 768 is directed to point $O_3$ (FIG. 25C). Sub-matrix 1070 (FIG. 27D) represents a green left view image of object 766 (download image $841'_D$), when the center of sensor assembly 768 directs to point $O_4$ (FIG. 25D). Sub-matrix 1072 (FIG. 27E) represents a red right view image of object 766 (download image $841'_E$), when the center of sensor assembly 768 directs to point $O_5$ (FIG. 25E). Sub-matrix 1074 (FIG. 27F) represents a red left view image of object 766 (download image $841'_F$), when the center of sensor assembly 768 directs to point $O_6$ (FIG. 25F).

According to FIG. 21A, a stereoscopic display unit (not shown) displays sub-matrices 1064, 1066, 1068, 1070, 1072 and 1074 in sequence. Sub-matrices 1064, 1068 and 1072 are the right side views of substantially the same area of object 766, which together compose a right side color image of the object 766. Sub-matrices 1066, 1070 and 1074 are the left side views of substantially the same area of object 766, which together compose a left side color image of the object 766. The stereoscopic display unit alternately displays the right view image and the left view image of substantially the same area of object 766. Thus, system 800 maintains a stable image of object 766, which does not exhibit any change in the location of object 766 as displayed on the stereoscopic display unit, despite the movement of sensor assembly 768 due to the vibrations of the human hand.

For example, image processor 838 selects sub-matrices 1064, 1068 and 1072 (FIGS. 27A, 27C and 27E, respectively), and the stereoscopic display (not shown), sequentially displays the same image in blue, green and red, respectively. Thus, the stereoscopic display presents a stable right side image of the object in full color, to the right eye. Similarly, the stereoscopic display sequentially displays sub-matrices 1066, 1070 and 1074 (FIGS. 27B, 27D and 27F, respectively), wherein the color of each sub-matrix sequentially changes from blue to green to red, respectively. In this manner, the stereoscopic display presents a stable left side image of the object in full color, to the left eye. Thus, the user views a stable full color stereoscopic image of the object, despite the movement of the endoscope due to the vibrations of the human hand.

It is noted that an RGB timing scheme can be employed. In this case, the stereoscopic display displays the sub-matrices in a sequence of right-red, left-green, right-blue, left-red, right-green and left-blue.

It is noted that the sequence of FIGS. 27A, 27B, 27C, 27D, 27E and 27F is cyclically repeated during the imaging process of the object. Other timing schemes can be employed where the download image trigger signal is used for acquiring a reading from movement detector 814, for the detected image. Examples for such timing schemes are illustrated in FIGS. 23, 24, and 21A.

It will be appreciated by persons skilled in the art that the present invention is not limited to what has been particularly shown and described here in above. Rather the scope of the present invention is defined only by the claims which follow.

In accordance with another aspect of the present invention, there is thus provided an edible capsule wirelessly incorporated with a control unit, for producing real time stereoscopic images of the digestive system of a patient while the capsule moves through the digestive system. The capsule further includes a plurality of compartments, for either dispensing chemical substances in the digestive system or collecting enteric substances from the digestive system, according to respective commands wirelessly transmitted from the control unit to the capsule.

Reference is now made to FIG. 28, which is a schematic illustration of an imaging system, generally referenced 880, constructed and operative in accordance with a further preferred embodiment of the present invention. System 880 includes a capsule 882 and a control unit 884. Capsule 882 includes a stereoscopic sensor assembly in the form of a lenticular lens layer 886 attached to a sensor array 888, a power supply 890, a processor 892, a memory unit 894, a transceiver 898, a light source 912, a light dispersing unit 918 and an optical assembly 910. Control unit 884 includes a transceiver 900, an image processing system 902 and a stereoscopic display 904. Lenticular lens layer 886, sensor array 888 and light source 912 are generally similar to lenticular lens layer 222 (FIG. 2), light sensor array 220 and light source 206, respectively, as described herein above. It is noted that stereoscopic display 904 can include stereoscopic goggles, a stereoscopic display unit, volumetric three-dimensional display, and the like.

Light dispersing unit 918 is in the form of an annular body made of a material which conveys beam of light there through, such as plastic, glass, and the like. Light dispersing unit 918 conveys and disperses the light beams which light source 912 emits. Light dispersing unit 918 surrounds the sensor assembly completely, thereby illuminating an object 908. Alternatively, the light dispersing unit can surround only part of the sensor assembly. Sensor array 888 detects light in gray scale. Alternatively, a different sensor array can be employed which detects light in a color scale. Light source 912 emits light beams in a predetermined range of wavelengths. Alternatively, a different light source can be employed, which emits at least two alternating beams of light, each in a different range of wavelengths.

Processor 892, memory unit 894 and transceiver 898 are interconnected through a common bus 906. Image processing system 902 of control unit 884 is connected to transceiver 900 and to stereoscopic display 904. Optical assembly 910 is located distally in capsule 882 in a line of sight between object 908 and lenticular lens layer 886.

Power supply 890 is a battery, an electrical power generator which draws power from the heat of the body of the patient, and the like, which provides electrical power to components located in capsule 882. Lenticular lens layer 886 separates a right side image and a left side image of object 908 for sensor array 888, and sensor array 888 sends a combined image (e.g., of the right and left side images) to processor 892. Processor 892 captures the image detected by sensor array 888 and processes each image, such as by performing data compression operations, and the like. For this purpose, processor 892 employs memory unit 894. Processor 892, then sends the processed data to transceiver 898. Transceiver 898 transmits the processed data, to image processing system 902 via transceiver 900.

Image processing system 902 processes the data received from transceiver 900, and produces two matrices respective of each of the right side and left side images of object 908. Image processing system 902, then produces video signals respective of the two matrices. Image processing system 902 provides the video signals to stereoscopic display 904, which in turn produces a stereoscopic image of object 908.

It is noted that according to this aspect of the present invention, capsule 882 provides a stereoscopic view of inner wall of digestive system of the patient, thus substantially assisting the treating physician to reach the correct and minimally invasive diagnosis. It is furthermore noted that according to another aspect of the present invention, processor 892 and memory unit 894 can be eliminated from capsule 882. In this case system 880 can still produce and display a stereoscopic image of object 908, although this stereoscopic image is of a lower quality.

Figure 29:
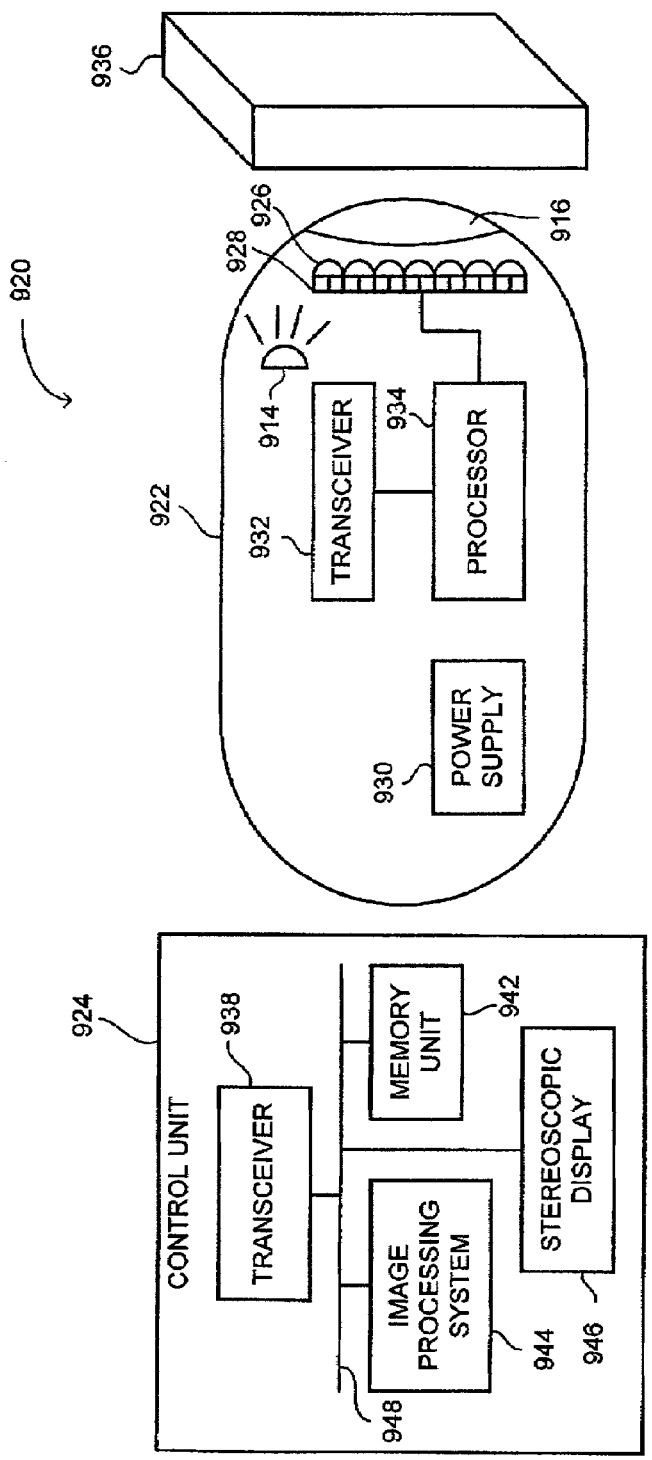
FIG. 29 is a schematic illustration of an imaging system, constructed and operative in accordance with another preferred embodiment of the present invention.

Reference is now made to FIGS. 29, which is a schematic illustration of an imaging system, generally referenced 920, constructed and operative in accordance with another preferred embodiment of the present invention. System 920 includes a capsule 922 and a control unit 924.

Capsule 922 includes a stereoscopic sensor assembly in the form of a lenticular lens layer 926 attached to a sensor array 928, a power supply 930, a processor 934, an optical assembly 916, a light source 914 and a transceiver 932. Control unit 924 includes a transceiver 938, a memory unit 942, an image processing system 944 and a stereoscopic display 946. Processor 934 is connected to sensor array 928 and to transceiver 932. Power supply 930 provides electrical power to all components located in capsule 922. Memory unit 942, image processing system 944 stereoscopic display 946 and transceiver 938 are interconnected via a common bus 948. Processor 934 receives data respective of the right side image and the left side image of an object 936 from sensor array 928, processes the data, and sends the data to transceiver 932. Transceiver 932 transmits the data to image processing system 944 via transceiver 938. Image processing system 944, in turn processes the data respective of the right side image and left side image, produces video signals respective of the right side image and the left side image of object 936, and transmits the video signals to stereoscopic display 946. Stereoscopic display 946, then provides a stereoscopic image of object 936.

It is noted that in this case capsule 922 includes a minimum number of components (i.e., lenticular lens layer 926, sensor array 928, power supply 930, transceiver 932, processor 934 and light source 914). Thus, capsule 922 can be much smaller in size than capsule 882 (FIG. 28), while providing the same information about the digestive system of the patient. As a result, the electrical power requirements of capsule 922 are typically lower than that of capsule 882, thus enabling a reduction in the size of power supply 930, compared with power supply 890. Therefore the physical dimensions of capsule 922 can be further smaller than those of capsule 882.

Figure 30:
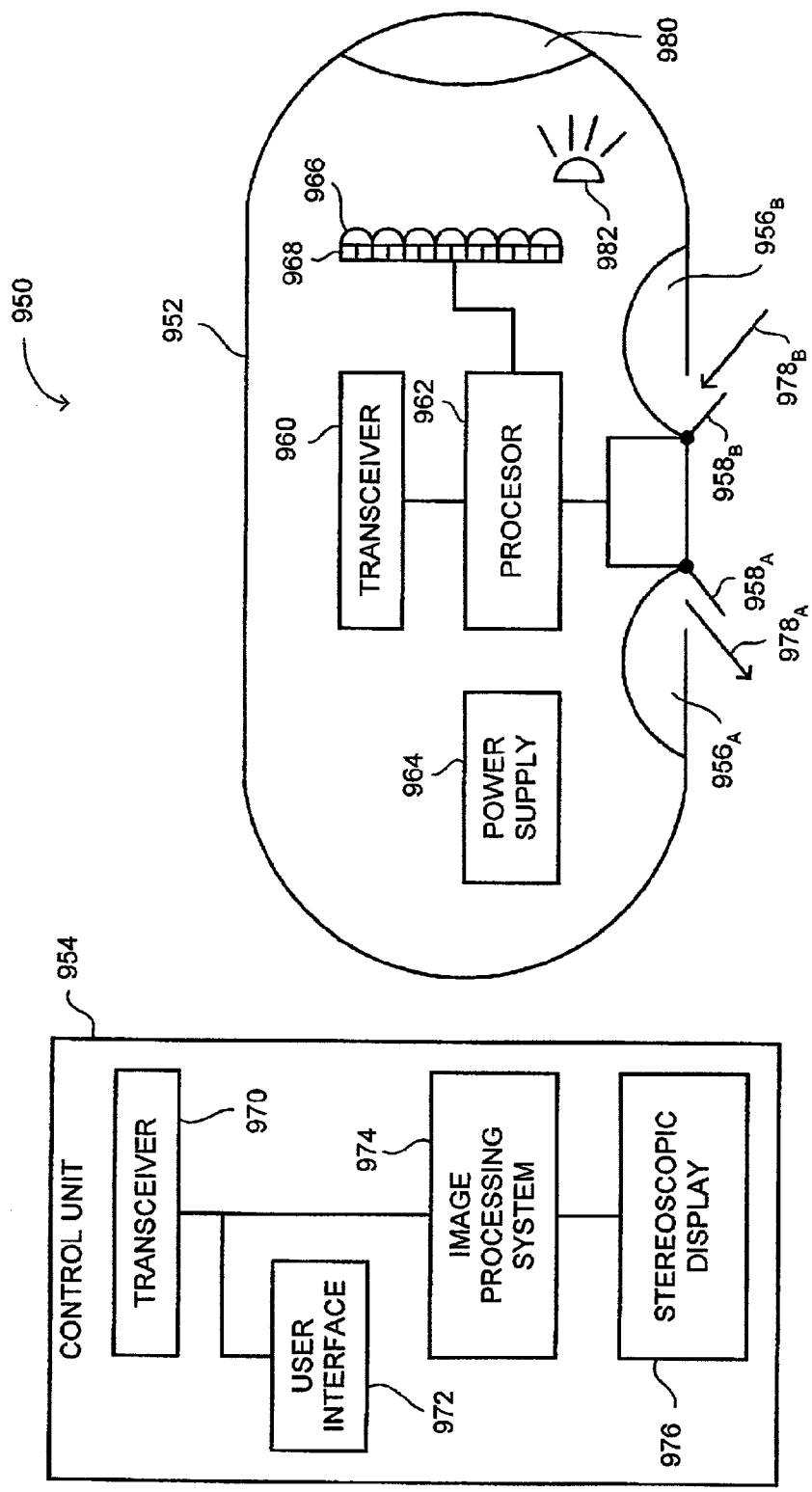
FIG. 30 is a schematic illustration of an imaging system, constructed and operative in, accordance with a further preferred embodiment of the present invention.

Reference is now made to FIG. 30, which is a schematic illustration of an imaging system, generally referenced 950, constructed and operative in accordance with a further preferred embodiment of the present invention. System 950 includes a capsule 952 and a control unit 954. Capsule 952 includes a plurality of dispensing compartments $956_A$, a plurality of collection compartments $956_B$, a transceiver 960, a processor 962, a power supply 964, a stereoscopic sensor assembly in the form of a lenticular lens layer 966 attached to a sensor array 968, a light source 982 and an optical assembly 980. Each of the dispensing compartment $956_A$ and collection compartment $956_B$ includes door mechanisms $958_A$ and $958_B$, respectively. Control unit 954 includes a transceiver 970, a user interface 972, an image processing system 974 and a stereoscopic display 976. Dispensing compartment $956_A$ is designed to release a medical substance into the digestive system, as shown by an arrow $978_A$. Collection compartment $956_B$ is designed to collect bodily substances from the digestive system, as shown by an arrow $978_B$.

Transceiver 960, processor 962, power supply 964, lenticular lens layer 966, sensor array 968 and optical assembly 980 are similar to transceiver 932 (FIG. 29), processor 934, power supply 930, lenticular lens layer 926, sensor array 928 and optical assembly 916, respectively. Transceiver 970, image processing system 974 and stereoscopic display 976 are likewise similar to transceiver 938, image processing system 944 and stereoscopic display 946, respectively. User interface 972 is an input device of the types known in the art, such as tactile, audio, visual, kinesthetic, and the like.

Processor 962 is connected to sensor array 968, transceiver 960, power supply 964 and each of door mechanisms $958_A$ and $958_B$. Image processing system 974 is connected to stereoscopic display 976, user interface 972 and transceiver 970.

Initially, when the patient ingests capsule 952, dispensing compartment $956_A$ and collection compartment $956_B$ are closed. Dispensing compartment $956_A$ contains a medical substance, which is to be dispensed in a selected location within the digestive system. On the other hand, collection compartment $956_B$ is initially empty, in order to collect a bodily substance from a selected location within the digestive system of the patient.

When door mechanism $958_A$ opens, the medical substance is released form dispensing compartment $956_A$. The amount of the medical substance released, can be controlled by controlling the opening time period of door mechanism $958_A$. Thus, in order to release a required volume of the medical substance, door mechanism $958_A$ is opened for a selected time period, and then immediately closed.

Likewise, when door mechanism $958_B$ is opened, the bodily substances in the vicinity of capsule 952 fill collection compartment $956_B$. Door mechanism $958_B$ can be left open for a selected period of time, in order to collect a selected amount of bodily substances. Door mechanism $958_B$ is then closed in order to keep the bodily substances-% within collection compartment $956_B$. At a later stage during the treatment, capsule 952 is retrieved from the patient, door mechanism $958_B$ is opened, and the collected bodily substances are removed from collection compartment $956_B$ for testing the collected bodily substances.

Processor 962 can direct either of door mechanisms $958_A$ or $958_B$ to open or close. Each of the door mechanisms $958_A$ and $958_B$ includes a movable element (not shown), such as a shape memory element, a bi-metallic element, a microelectromechanical system (MEMS), and the like, which alternately opens and closes the respective door mechanism.

When capsule 952 moves within the digestive system of the patient, the physician views the stereoscopic image of the internal wall of the digestive system in real time, via stereoscopic display 976. When the physician determines that the medical substance has to be dispensed at a selected location, as viewed via stereoscopic display 976, she directs door mechanism $958_A$ via user interface 972, to open. The physician can direct user interface 972 to leave door mechanism $958_A$ open, for a selected period of time in order to dispense a selected volume of the medical substance.

When user interface 972 receives a command from the physician to open door mechanism $958_A$, user interface 972 sends a respective signal to transceiver 970. Transceiver 970 in turn transmits the signal to transceiver 960, and processor 962 directs door mechanism $958_A$ to open according to another signal received from transceiver 960.

When the physician determines that bodily substances have to be collected from a selected location, for example, as viewed via stereoscopic display 976, she directs user interface 972 to open door mechanism $958_B$. Door mechanism $958_B$ is closed after a predetermined time, either manually or automatically, during which a controlled amount of bodily substances enter collection compartment $956_B$ and fill collection compartment $956_B$. The physician directs capsule 952 to activate door mechanism $958_B$ as described herein above in conjunction with activation of door mechanism $958_A$.

It is noted that capsule 952 can include a plurality of dispensing compartments $956_A$ and a plurality of collection compartments $956_B$. Thereby, the physician can direct capsule 952 to dispense different or the same medical substances, at one or different locations within the digestive system of the patient. For this purpose, processor 962 includes therein the addresses of each of the plurality of dispensing compartments. Thus, user interface 972 can associate an activation command (i.e., open or close) with a selected dispensing compartment. Likewise, processor 962 includes the addresses of each of the collection compartments, wherein user interface 972 can associate an activation command with a selected collection compartment.

Figure 31:
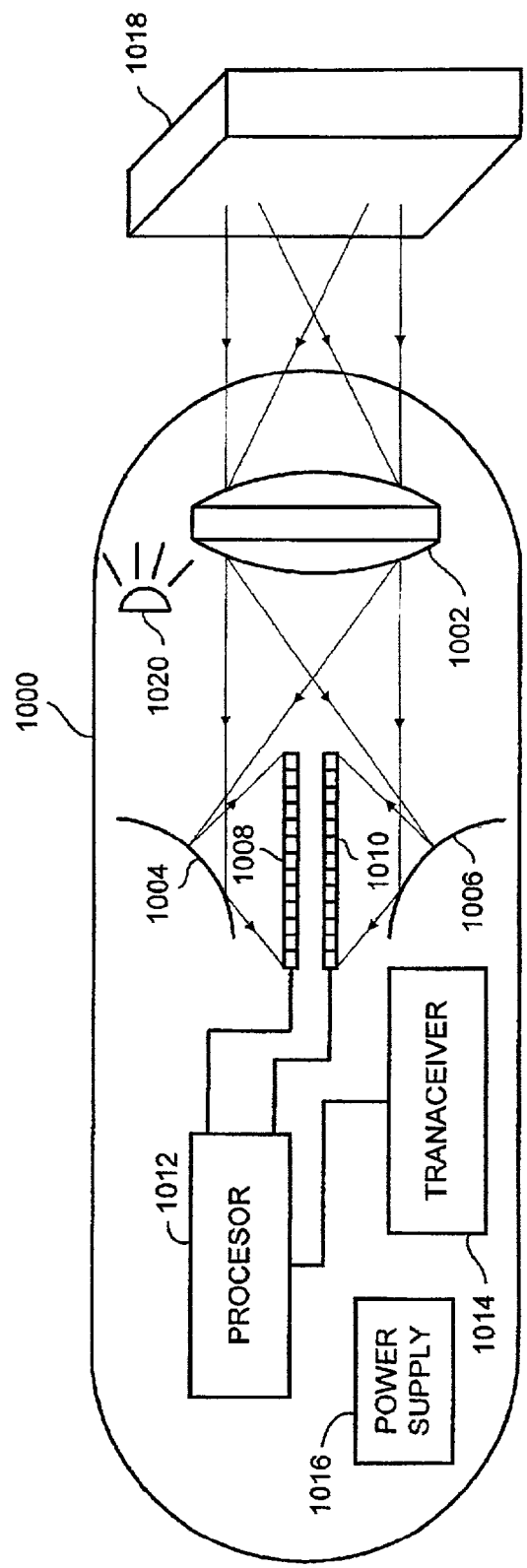
FIG. 31 is a schematic illustration of a capsule, constructed and operative in accordance with another preferred embodiment of the present invention.

Reference is now made to FIG. 31, which is a schematic illustration of a capsule, generally referenced 1000, constructed and operative in accordance with another preferred embodiment of the present invention. Capsule 1000 includes an optical assembly 1002, an upper mirror 1004, a lower mirror 1006, an upper sensor array 1008, a lower sensor array 1010, a processor 1012, a transceiver 1014, a light source 1020 and a power supply 1016. Upper mirror 1004 and lower mirror 1006 are each convex type mirrors. In general, these mirrors are each designed to project the image received from the optical assembly, onto the respective sensor array, and hence can assume other shapes, depending on the optical geometry of the system.

The detecting surfaces of upper sensor array 1008 and lower sensor array 1010 face opposite directions. Upper mirror 1004 faces the detecting surface of upper sensor array 1008, and lower mirror 1006 faces the detecting surface of lower sensor array 1010. Optical assembly 1002 is located between lower mirror 1006, upper mirror 1004, and an object 1018 such that optical assembly 1002 directs light beams from object 1018 to lower mirror 1006 and upper mirror 1004. Upper sensor array 1.008 and lower sensor array 1010 are each connected to processor 1012. Processor 1012 is further connected to transceiver 1014.

Optical assembly 1002 directs the light beams from the upper view of object 1018, toward lower mirror 1006. Likewise, optical assembly 1002 directs the light beams from the lower view of object 1018, toward upper mirror 1004. Lower mirror 1006, then directs the upper view image of object 1018 toward lower sensor array 1010, and upper mirror 1004 directs the lower view image of object 1018 toward upper sensor array 1008. Thus, lower sensor array 1010 detects the upper view image of object 1018 and upper sensor array 1008 detects the lower view image of object 1018.

Processor 1012 processes the data which upper sensor array 1008 and lower sensor array 1010 produce, such as by performing data compression operations, discarding redundant data, and the like. Transceiver 1014 transmits the processed data to an image processing system (not shown) via a different transceiver (not shown). The image processing system produces video signals respective of the processed data, and a stereoscopic display (not shown) displays a stereoscopic image of object 1018. It is noted that the light beam configuration illustrated in FIG. 31 is only an example (i.e., upper mirror 1004 and lower mirror 1006 are not restricted to convex type mirrors). Thus, according to this aspect of the present invention, other types of mirrors can be employed.

Figure 32A:
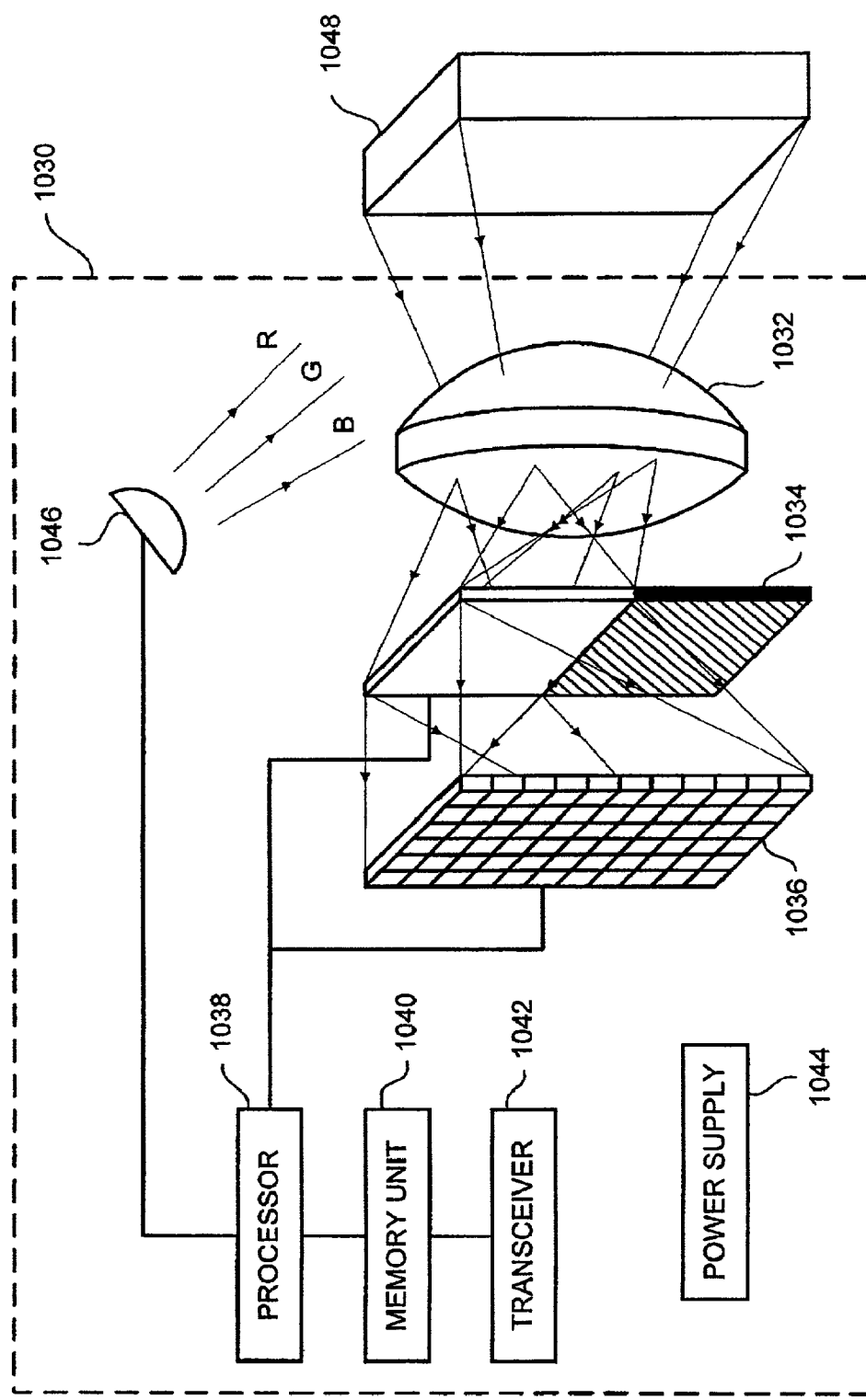
FIG. 32A is a schematic illustration of a capsule, constructed and operative in accordance with a further preferred embodiment of the present invention.
Figure 32B:
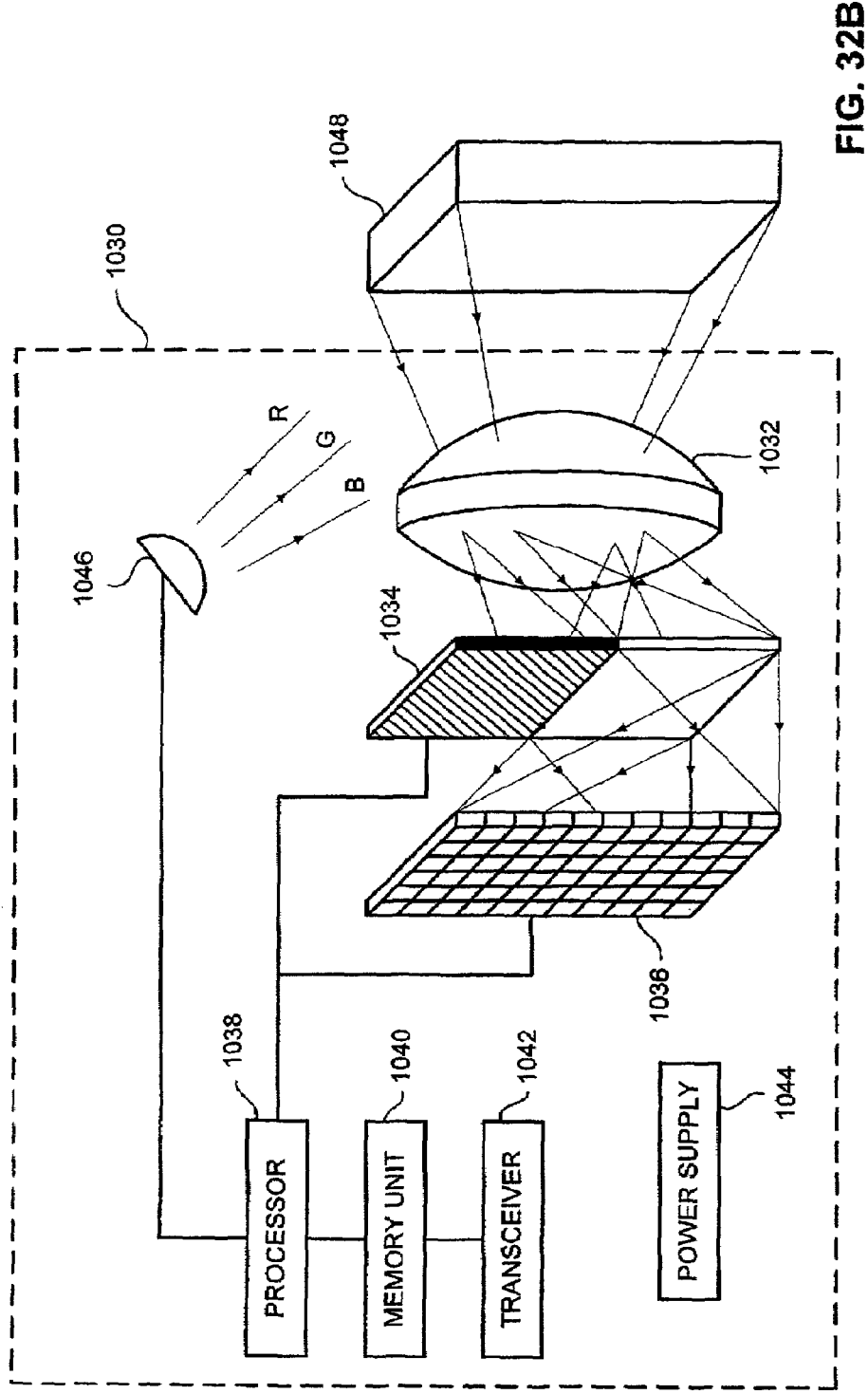
FIG. 32B is an illustration of the capsule of FIG. 32A, in a different detection mode.

Reference is now made to FIGS. 32A and 32B. FIG. 32A is a schematic illustration of a capsule, generally referenced 1030, constructed and operative in accordance with a further preferred embodiment of the present invention. FIG. 32B is an illustration of the capsule of FIG. 32A, in a different detection mode.

Capsule 1030 includes a lens 1032, a stereoscopic sensor assembly in the form of a multiple aperture 1034 and a sensor array 1036, a processor 1038, a memory unit 1040, a transceiver 1042, an illumination unit 1046 and a power supply 1044. Multiple aperture 1034, sensor array 1036, processor 1038 and illumination unit 1046 are substantially similar to multiple aperture 804 (FIG. 20A), image detector 812, controller 834 and illumination unit 830, respectively, as described herein above.

With reference to FIG. 32A, illumination unit 1046 illuminates an object 1048, and lens 1032 focuses the light beams reflected by object 1048 on multiple aperture 1034. The lower portion of multiple aperture 1034 is closed, thus sensor array 1036 detects the upper view of object 1048. With reference to FIG. 32B, the upper portion of multiple aperture 1034 is closed, wherein sensor array 1036 detects the lower view of object 1048. The upper and lower portions of multiple aperture 1034 alternately open and close, thereby allowing sensor array 1036 to detect alternately the upper and lower views of object 1048.

Processor 1038 operates multiple aperture 1034, sensor array 1036 and illumination unit 1046 as described herein above in connection with FIG. 20A. Processor 1038 receives a sequence of images of object 1048, for example as illustrated in FIG. 21A, from sensor array 1036 and sequentially stores the images in memory unit 1040. When memory unit 1040 contains a predetermined number of the sequential images, memory unit 1040 sends these images to transceiver 1042. Transceiver 1042 sends the images to an image processing system (not shown) via a different transceiver (not shown). The image processing system produces video signals respective of the images, and an stereoscopic display (not shown) displays a stereoscopic image of object 1048. It is noted that based on the type of illumination unit 1046 (i.e., color or monochrome), the stereoscopic display can display either a color or a monochromatic stereoscopic image of object 1048.

The invention claimed is:

1. System for producing a stereoscopic image of an object, and displaying the stereoscopic image, the system comprising:
    a capsule; and
    a control unit;
    said capsule comprising:
        a sensor assembly;
        a processor connected to said sensor assembly;
        a capsule transceiver connected to said processor;
        at least one dispensing compartment containing a medical substance and comprising a door mechanism, and each of said door mechanisms is connected to said processor, wherein each of said at least one dispensing compartments releases a selected amount of said medical substance according to a command provided by said processor to said door mechanism;
        a light source; and
        a power supply for supplying power to said capsule transceiver, said processor, said light source and to said sensor assembly;
    wherein, said sensor assembly detects said stereoscopic image, said processor captures said stereoscopic image, said capsule transceiver transmits said stereoscopic image to said control unit transceiver and said image processing system processes said stereoscopic image.

2. System for producing a stereoscopic image of an object, and displaying the stereoscopic image, the system comprising:
    a capsule; and
    a control unit;
    said capsule comprising:
        a sensor assembly;
        a processor connected to said sensor assembly;
        at least one collecting compartment collecting a bodily substance and comprising a door mechanism, and each of said door mechanisms is connected to said processor, wherein each of said at least one collecting compartments collects a selected amount of said bodily substance according to a command which said processor provides said door mechanism;
        a light source;
        a capsule transceiver connected to said processor;
        a power supply for supplying power to said capsule transceiver, said processor, said light source and to said sensor assembly;
    wherein, said sensor assembly detects said stereoscopic image, said processor captures said stereoscopic image, said capsule transceiver transmits said stereoscopic image to said control unit transceiver and said image processing system processes said stereoscopic image.

3. System for producing a stereoscopic image of an object, and displaying the stereoscopic image, the system comprising:
    a capsule; and
    a control unit;
    said capsule comprising:
        a sensor assembly comprising:
        a lower light sensor array connected to said processor;
        an upper light sensor array connected to said processor, an upper light sensor array detecting surface faces a direction opposite to the direction of a lower light sensor array detecting surface;
        a lower mirror facing said lower light sensor array detecting surface;
        an upper mirror facing said upper light sensor array detecting surface; and
        an optical assembly located between said lower mirror, said upper mirror and said object for directing light beams from said object to said lower mirror and to said upper mirror, and
    wherein each of said lower light sensor array and said upper light sensor array includes a plurality of light sensors, and
    wherein said optical assembly directs at least one light beam from a first portion of said object to said lower mirror, and said optical assembly directs at least one light beam from a second portion of said object to said upper mirror, and
    wherein said lower mirror reflects said at least one light beam from said first portion to said lower light sensor array detecting surface, said upper mirror reflects said at least one light beam from said second portion to said upper light sensor detecting surface, and
    wherein said lower light sensor array detects an image of said first portion and said upper light sensor array detects an image of said second portion;
        a processor connected to said sensor assembly;
        a capsule transceiver connected to said processor;
        a power supply for supplying power to said capsule transceiver, said processor, said light source and to said sensor assembly;
    wherein, said sensor assembly detects said stereoscopic image, said processor captures said stereoscopic image, said capsule transceiver transmits said stereoscopic image to said control unit transceiver and said image processing system processes said stereoscopic image.

4. The system according to claim 3, wherein said light source produces at least two alternating beams of light, each said alternating beams of light characterized as being in a different range of wavelengths.

5. The system according to claim 4, wherein each of said different ranges of wavelengths associated with said light source, is selected from the list consisting of:
    substantially visible red color light;
    substantially visible green color light;
    substantially visible blue color light;
    substantially visible cyan color light;
    substantially visible yellow color light;
    substantially visible magenta color light;

substantially infra-red light;
substantially ultra-violet light; and
visible light.

6. The system according to claim 3, wherein said light source produces light in a predetermined range of wavelengths.

7. The system according to claim 3, wherein said lower light sensor array includes at least two groups of sensors, the sensors of each said group detect light in a different range of wavelengths.

8. The system according to claim 7, wherein each said different ranges of wavelengths associated with said sensors, is selected from the list consisting of:
substantially visible red color light;
substantially visible green color light;
substantially visible blue color light;
substantially visible cyan color light;
substantially visible yellow color light;
substantially visible magenta color light;
substantially infra-red light;
substantially ultra-violet light; and
visible light.

9. The system according to claim 3, wherein said upper light sensor array includes at least two groups of sensors, the sensors of each said group detect light in a different range of wavelengths.

10. The system according to claim 9, wherein each said different ranges of wavelengths associated with said sensors, is selected from the list consisting of:
substantially visible red color light;
substantially visible green color light;
substantially visible blue color light;
substantially visible cyan color light;
substantially visible yellow color light;
substantially visible magenta color light;
substantially infra-red light;
substantially ultra-violet light; and
visible light.

11. The system according to claim 3, wherein said lower light sensor array includes a plurality of sensors, each said sensors detects light in a predetermined range of wavelengths.

12. The system according to claim 11, wherein each said predetermined ranges of wavelengths associated with said sensors, is selected from the list consisting of:
substantially visible red color light;
substantially visible green color light;
substantially visible blue color light;
substantially visible cyan color light;
substantially visible yellow color light;
substantially visible magenta color light;
substantially infra-red light;
substantially ultra-violet light; and
visible light.

13. The system according to claim 3, wherein said upper light sensor array includes a plurality of sensors, each said sensors detects light in a predetermined range of wavelengths.

14. The system according to claim 13, wherein each said predetermined ranges of wavelengths associated with said sensors, is selected from the list consisting of:
substantially visible red color light;
substantially visible green color light;
substantially visible blue color light;
substantially visible cyan color light;
substantially visible yellow color light;
substantially visible magenta color light;
substantially infra-red light;
substantially ultra-violet light; and
visible light.

15. The system according to claim 3, wherein said lower light sensor array is a color red-green-blue (RGB) sensor array.

16. The system according to claim 3, wherein said upper light sensor array is a color red-green-blue (RGB) sensor array.

17. The system according to claim 3, wherein said lower light sensor array is a color cyan-yellow-magenta-green (CYMG) sensor array.

18. The system according to claim 3, wherein said upper light sensor array is a color cyan-yellow-magenta-green (CYMG) sensor array.

19. The system according to claim 3, wherein said lower mirror is convex.

20. The system according to claim 3, wherein said upper mirror is convex.

* * * * *